(12) United States Patent
Talton

(10) Patent No.: US 7,063,748 B2
(45) Date of Patent: Jun. 20, 2006

(54) METHODS FOR COATING PARTICLES AND PARTICLES PRODUCED THEREBY

(75) Inventor: James D. Talton, Gainesville, FL (US)

(73) Assignee: Nanotherapeutics, Inc., Alachua, FL (US)

( * ) Notice: Subject to any disclaimer, the term of this patent is extended or adjusted under 35 U.S.C. 154(b) by 0 days.

(21) Appl. No.: 10/095,585

(22) Filed: Mar. 13, 2002

(65) Prior Publication Data

US 2002/0106461 A1  Aug. 8, 2002

Related U.S. Application Data

(63) Continuation of application No. 09/588,208, filed on Jun. 6, 2000, now Pat. No. 6,406,745.

(60) Provisional application No. 60/137,733, filed on Jun. 7, 1999, provisional application No. 60/138,006, filed on Jun. 7, 1999.

(51) Int. Cl.
*C23C 14/28* (2006.01)

(52) U.S. Cl. .................. 118/716; 118/722; 118/725; 118/726; 118/729

(58) Field of Classification Search ................ 118/716, 118/722, 725, 726, 729; 366/111–113, 124–126
See application file for complete search history.

(56) References Cited

U.S. PATENT DOCUMENTS

| | | | | |
|---|---|---|---|---|
| 3,318,163 A | * | 5/1967 | Matson | 74/87 |
| 3,429,295 A | * | 2/1969 | Shapiro | 118/716 |
| 3,517,644 A | * | 6/1970 | Baer | 118/716 |
| 3,584,249 A | * | 6/1971 | Murphy | 310/81 |
| 3,648,983 A | * | 3/1972 | Campbell | 366/116 |
| 3,817,495 A | * | 6/1974 | Uebel et al. | 366/126 |
| 3,945,246 A | * | 3/1976 | Wadensten | 73/666 |
| 4,046,712 A | | 9/1977 | Cairns et al. | |
| 4,302,311 A | * | 11/1981 | Lowe et al. | 204/192.13 |
| 4,348,363 A | * | 9/1982 | Akiyama et al. | 422/192 |
| 4,656,056 A | | 4/1987 | Leuenberger | |
| 4,848,673 A | | 7/1989 | Masuda et al. | |
| 4,940,523 A | * | 7/1990 | Takeshima | 204/192.12 |
| 4,991,541 A | * | 2/1991 | Sugata et al. | 118/716 |
| 5,154,567 A | * | 10/1992 | Baker et al. | 73/665 |
| 5,209,564 A | * | 5/1993 | Manci et al. | 366/124 |
| 5,242,706 A | | 9/1993 | Cotell et al. | |
| 5,288,504 A | | 2/1994 | Versic | 424/497 |
| 5,288,528 A | | 2/1994 | Blanchet-Fincher | |
| 5,399,363 A | | 3/1995 | Liversidge et al. | |
| 5,399,636 A | | 3/1995 | Alt et al. | |

(Continued)

FOREIGN PATENT DOCUMENTS

DE  4239244 A1  7/1994

(Continued)

OTHER PUBLICATIONS

Fitz-gerald, Mat. Res. Soc. Symp. vol. 526, pp. 105-110, Apr. 13-16, 1998.*

(Continued)

*Primary Examiner*—Richard Bueker
(74) *Attorney, Agent, or Firm*—Finnegan, Henderson, Farabow, Garrett & Dunner, L.L.P.

(57) ABSTRACT

Methods of coating core materials by providing target materials and core materials; ablating the target materials to form ablated particulate target materials; and coating the core materials with said ablated particulate target materials; wherein the method is performed at a pressure of about 10 Torr or higher. Methods of coating particles with nanometer to multiple nanometer thick coatings in atmospheric pressure, and using pneumatic fluidization, are also provided.

21 Claims, 22 Drawing Sheets

U.S. PATENT DOCUMENTS

| | | | |
|---|---|---|---|
| 5,437,889 A | 8/1995 | Jones | |
| 5,456,917 A | 10/1995 | Wise et al. | |
| 5,466,468 A | 11/1995 | Schneider et al. | |
| 5,470,388 A * | 11/1995 | Goedicke et al. | 118/716 |
| 5,489,449 A | 2/1996 | Umeya et al. | |
| 5,536,508 A | 7/1996 | Canal et al. | |
| 5,543,158 A | 8/1996 | Gref et al. | |
| 5,580,579 A | 12/1996 | Ruddy et al. | |
| 5,622,567 A * | 4/1997 | Kojima et al. | 118/726 |
| 5,641,515 A | 6/1997 | Ramtoola | |
| 5,641,745 A | 6/1997 | Ramtoola | |
| 5,656,016 A | 8/1997 | Ogden | |
| 5,693,340 A | 12/1997 | Harth et al. | |
| 5,697,899 A | 12/1997 | Hillman et al. | |
| 5,702,716 A | 12/1997 | Dunn et al. | |
| 5,725,871 A | 3/1998 | Illum | |
| 5,756,353 A | 5/1998 | Debs | |
| 5,766,557 A | 6/1998 | Luy et al. | |
| 5,770,219 A | 6/1998 | Chiang et al. | |
| 5,779,708 A | 7/1998 | Wu | |
| 5,780,045 A | 7/1998 | McQuinn et al. | |
| 5,783,208 A | 7/1998 | Venkateshwaran et al. | |
| 5,792,451 A | 8/1998 | Sarubbi et al. | |
| 5,797,898 A | 8/1998 | Santini, Jr. et al. | |
| 5,804,212 A | 9/1998 | Illum | |
| 5,814,344 A | 9/1998 | Tice et al. | |
| 5,820,833 A | 10/1998 | Kawamura | |
| 5,849,265 A | 12/1998 | Li-Bovet et al. | |
| 5,922,306 A | 7/1999 | Akehurst et al. | |
| 6,001,336 A | 12/1999 | Gordon | |
| 6,025,036 A | 2/2000 | McGill et al. | |
| 6,074,135 A | 6/2000 | Tapphorn et al. | 406/46 |
| 6,087,003 A | 7/2000 | Benoit et al. | |
| 6,197,120 B1 * | 3/2001 | David | 118/716 |
| 6,274,207 B1 * | 8/2001 | Balkus et al. | 427/596 |
| 6,984,404 B1 | 1/2006 | Talton et al. | |

FOREIGN PATENT DOCUMENTS

| | | |
|---|---|---|
| WO | 90/02546 | 3/1990 |
| WO | WO 98 53 767 | 12/1998 |
| WO | 99/47726 | 9/1999 |
| WO | 00/28969 | 5/2000 |

OTHER PUBLICATIONS

Fitz-gerald, Applied Physics Letters, vol. 72, No. 15, pp. 1838-1839, Apr. 13, 1998.*

Balkus, Chemistry of Materials, vol. 11, No. 2, pp. 189-191, published on the web, Jan. 23, 1999.*

Chrisey, Pulsed Laser Deposition of Thin Films, John Wiley & sons, New York, 1994, pp. 36-38.*

Chrisey, Pulsed Laser Deposition of Thin Films, John Wiley & sons, 1994, pp. 13-16 and 48-49.*

Yoshida, Appl. Phys. Lett. 68 (13), Mar. 25, 1996, pp. 1772-1774.*

Chrisey, Pulsed Laser Deposition of Thin Films, John Wiley & Sons, Inc., 1994, pp. 184-.*

Hardy, et al., "Sustained Release Drug Delivery to the Lungs," *Clin Pharmacokinet* Jul. 2000:39(1).

Talton, et al., "Nano-Thin Coatings for Improved Lung Targeting of Glucocorticoid Dry Powders: *In-Vitro* and *in-vivo* Characteristics," *Respiratory Drug Delivery, VII,* 2000, p. 67-74.

Sato, et al., Porous Biodegradable Microspheres for Controlled Drug Delivery. I. Assessment of Processing Conditions and Solvent Removal Techniques, *Pharmaceutical Research,* vol. 5, No. 1, 1988, p. 21-30.

Curt Thies, "Microcapsules as Drug Delivery Devices," *Critical Review in Biomedical Engineering,* vol. 8, Issue 4, 1982. p. 335-383.

Bourlais, et al., "Ophthalmic Drug Delivery Systems—Recent Advances," *Progress in Retinal and Eye Research,* vol. 17, No. 1, pp. 33-58, 1998.

Talton, James D., Ph.D. Thesis, University of Florida, 1999.

Hausberger, et al., "Characterization of biodegradable Poly(D.L-lactide-co-glycolide) Polymers and Microspheres," *Journal of Pharmaceutical & Biomedical Analysis,* vol. 13, No. 6, pp. 747-760 (1995).

Phadke, et al., "Laser-Assisted Deposition of Preformed Mesoscopic Systems," *Materials Science and Engineering,* C 5 237-241 (1998).

Piqué, et al., "Growth of Organic Thin Films by the Matrix Assisted Pulsed Laser Evaporation (MAPLE) Technique," *Thin Solid Films,* 355-56 (1999) 536-541.

Grace and Matsen, *Fluidization,* Plenum Press (table of contents only).

Gunjan Agarwal, Ratna S. Phadke, "Laser Assisted Deposition of Supramolecular Organizates on Solid Surfaces," *Material Science and Engineering,* C 6 (1998) 13-17.

Chapters 15 and 16 from *Modern Pharmaceutics,* p. 605-671.

Burton and Schanker, "Absorption of Corticosteriods from the Rat Lung," *Steriods,* vol. 23, No. 5, May 1974.

Conti, et al., "Use of Polylactic Acid for the Preparation of Microparticulate Drug Delivery Systems," *J. Microencapsulation,* 1992, vol. 9, No. 2, 153-166.

Fielding and Abra, "Factors Affecting the Release Rate of Terbutaline from Liposome Formulations After Intratracheal Instillation in the Guinea Pig," *Pharmaceutical Research,* vol. 9, No. 2, 1992.

Glatt, "Multi-Purpose Fluid Bed Processing," *Product Literature,* 1998.

Göpferich, et al., "Development and Characterization of Microencapsulated Microspheres," *Pharmaceutical Research,* vol. 11, No. 11, 1994, 1568-1574.

Herdan, G., title page to "Small Particle Statistics," Second Edition, Butterworths, London, 1960.

Hochhaus, et al., "Pharmacokinetic/Pharmacodynamic Aspects of Aerosol Therapy using Glucocorticoids as a Model," *J. Clin Pharmacol,* 1997, 881-892.

Hochhaus, et al., "Assessment of Glucocorticoid Lung Targeting by *ex-Vivo* Receptor Binding Studies in Rats," *Pharmaceutical Research,* vol. 1,2 No. 1, 1995, 134-137.

Kawashima, et al., "A New Powder Design Method to Improve Inhalation Efficiency of Pranlukast Hydrate Dry Powder Aerosols by Sdurface Modification with Hydroxypropylmethylcellulose Phthalate Nanospheres," *Pharmaceutical Research,* vol. 15, No. 11, 1998, 1748-1752.

Page 36-39 from Kodas and Hampden-Smith, "Aerosol Processing of Materials," Wiley-VCH, New York, 1999.

Mathiowitz, et al., "Biologically Erodable Microsphere as Potential Oral Drug Delivery Systems," *Nature,* vol. 386, 1997, 410-414.

Newman, et al., "Efficient Delivery to the Lungs of Flunisolide Aerosol from a New Portable Hand-Held Multidose Nebulizer," *J. Pharm. Sci.,* vol. 85, No. 9, 1996, 960-964.

Ogale, S.B., "Deposition of Polymer Films by Laser Ablation," *Pulsed Laser Deposition of Thin Films,* 1994, Chapter 25, p. 567-579.

Schreier, et al., "Pulmonary Delivery of Liposomes," *Journal of Controlled Release*, 24 (1993) 209-223.

Takenaga, et al., "Microparticle Resins as a Potential Nasal Drug Delivery System for Insulin," *Journal of Controlled Release*, 52 (1998) 81-87.

Tremblay, et al. "Liposomal Dexamethasone Effectiveness in the Treatment of Hypersensitivity Pneumonitis in Mice," *European Journal of Clinical Investigation*, 23 (1993) 656-661.

Vidgren, et al., "A Study of $^{99m}$ Technetium-Labelled Beclomethasone Dipropionate Dilauroylphosphatidylcholine Liposome Aerosol in Normal Volunteers," *International Journal of Pharmaceutics*, 115 (1995) 209-216.

Zeng, et al., "The Controlled Delivery of Drugs to the Lung," *International Journal of Pharmaceutics*, 124 (1995) 149-164.

Schreier, et al., "Thermodynamic and Kinetic Aspects of the Interaction of Triamcinolone Acetonide with Liposomes," *Proceed. Intern. Symp. Control. Rel. Bioact. Mater.*, 21 (1994), p. 228-229.

Mutschler, et al., "Basic Principles and Therapeutic Aspects," *Drug Actions*, 1995, p. 286-287.

Manekar, et al., "Microencapsulation of Propranolol Hydrochloride by the Solvent Evaporation Technique," *J. Microencapsulation*, 1992, vol. 9, No. 1, 63-66.

Huang, et al., "An AM1-based Model for the Estimation of the Relative Binding Affinity for Glucocorticoids," *1$^{st}$ Drug Optimizaiton via Retrometabolism Conference*, Amelia Island: Die Pharmazie, 1997, abstract only.

Leach, et al., "Oligolactic Acid (OLA) Biomatrices for Sustained Release of Asthma Therapeutics," *Respiratory Drug Delivery IV*, p. 75-81, (2000).

Fitz-Gerald et al., "Novel Method for the Synthesis of Thin Film Coatings on Particulate Materials," *J. Mater. Res.*, 14:3281-3291 (1999).

Rau et al., "Synthesis and Characterization of Cross-Linked Silicone Thin Films by Pulsed Laser Ablation Deposition (PLAD)," *Mat. Res. Innovat.*, 5:162-169 (2002).

\* cited by examiner

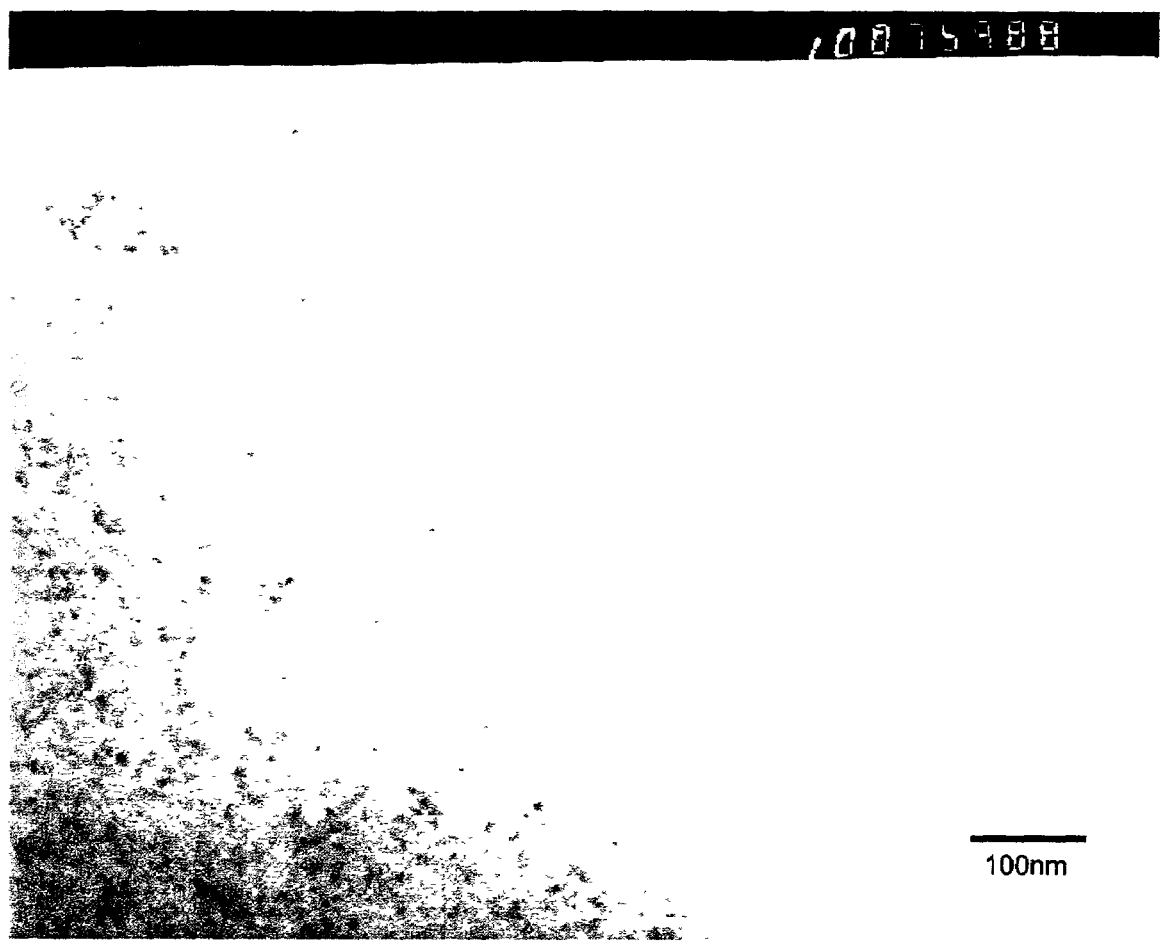
Figure 3   TEM image of deposited nanoparticles film at atmospheric pressure (scale 100,000 times).

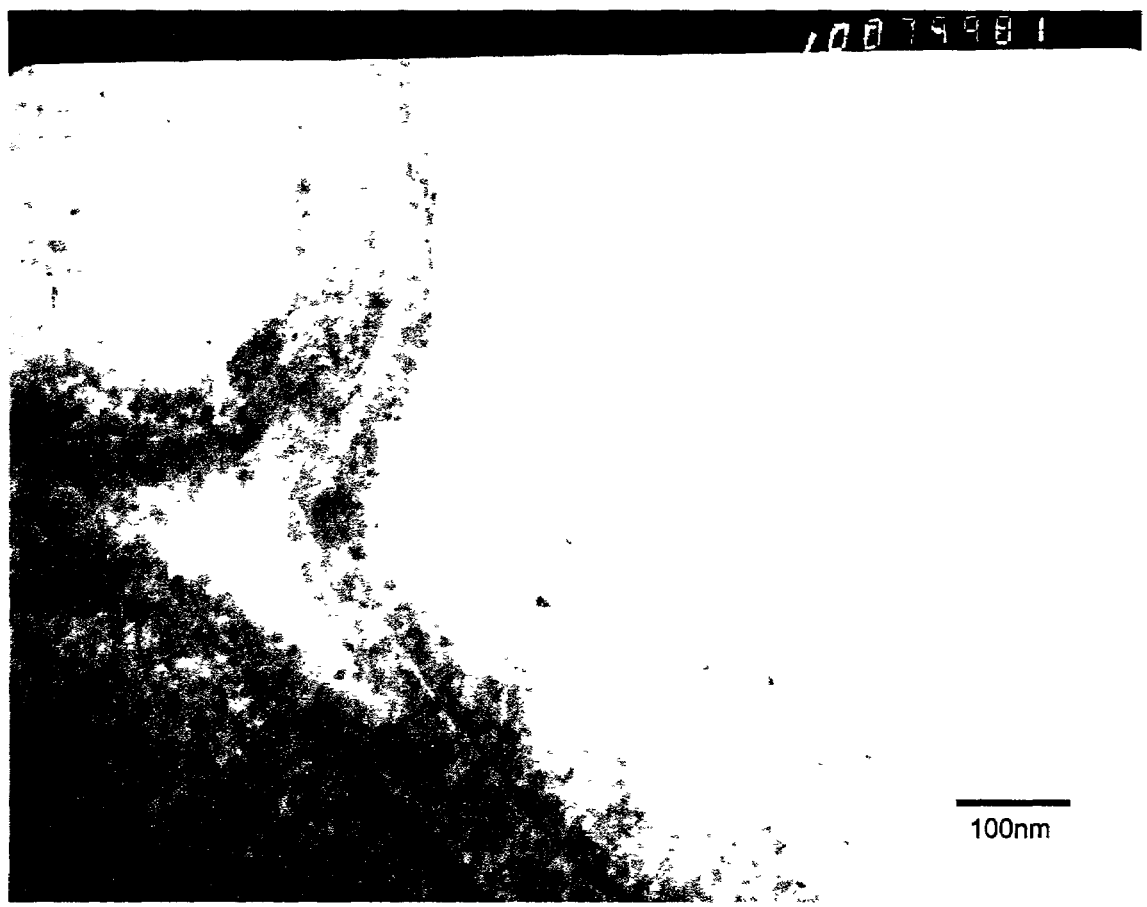
Figure 4　　TEM image of deposited nanoparticles film at atmospheric pressure (scale 100,000 times).

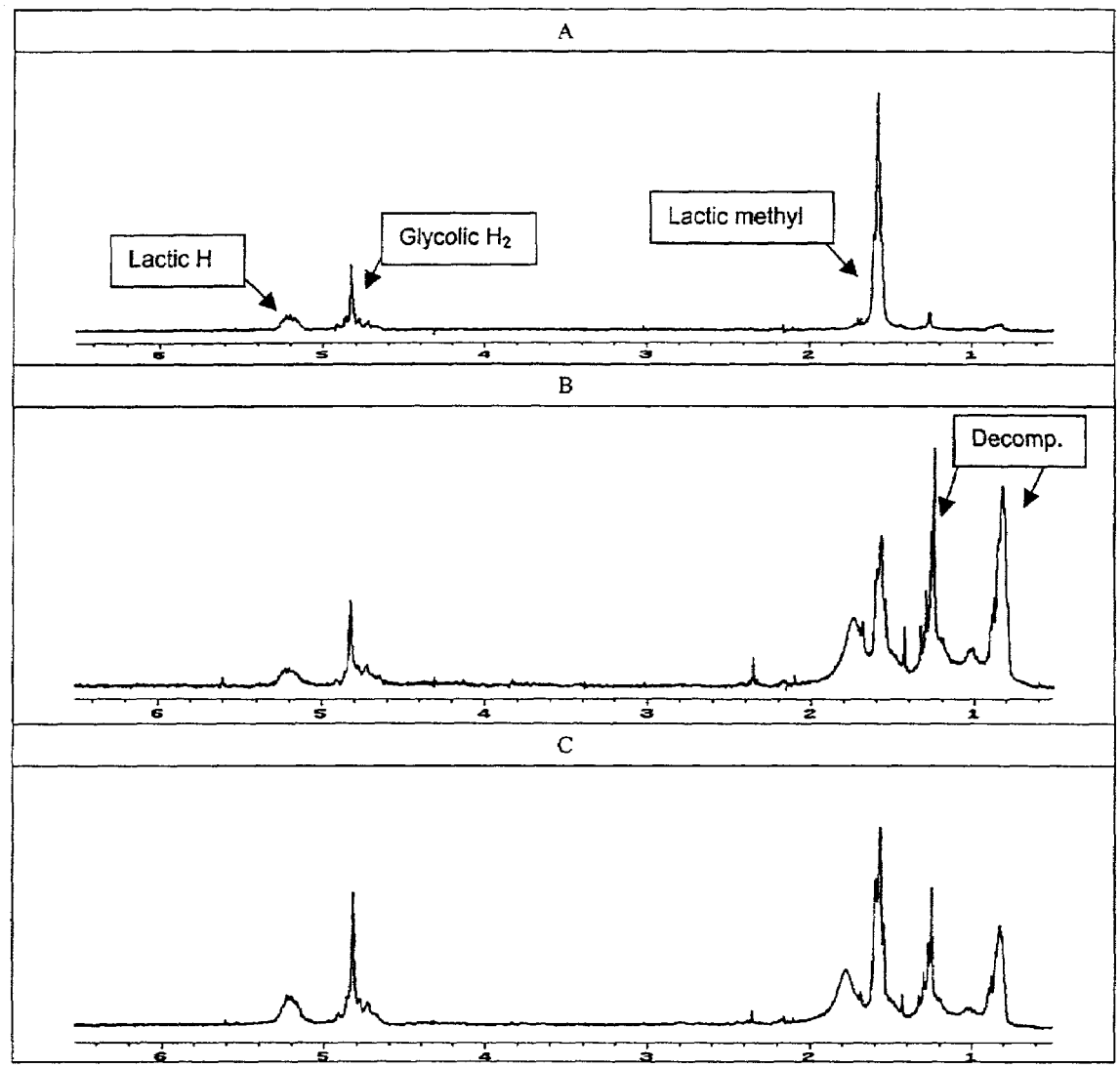
Figure 5  1H-NMR spectra of A) original PLGA, B) deposited PLGA at 200 mJ at atmospheric pressure, and C) near atmospheric pressure (10 Torr).

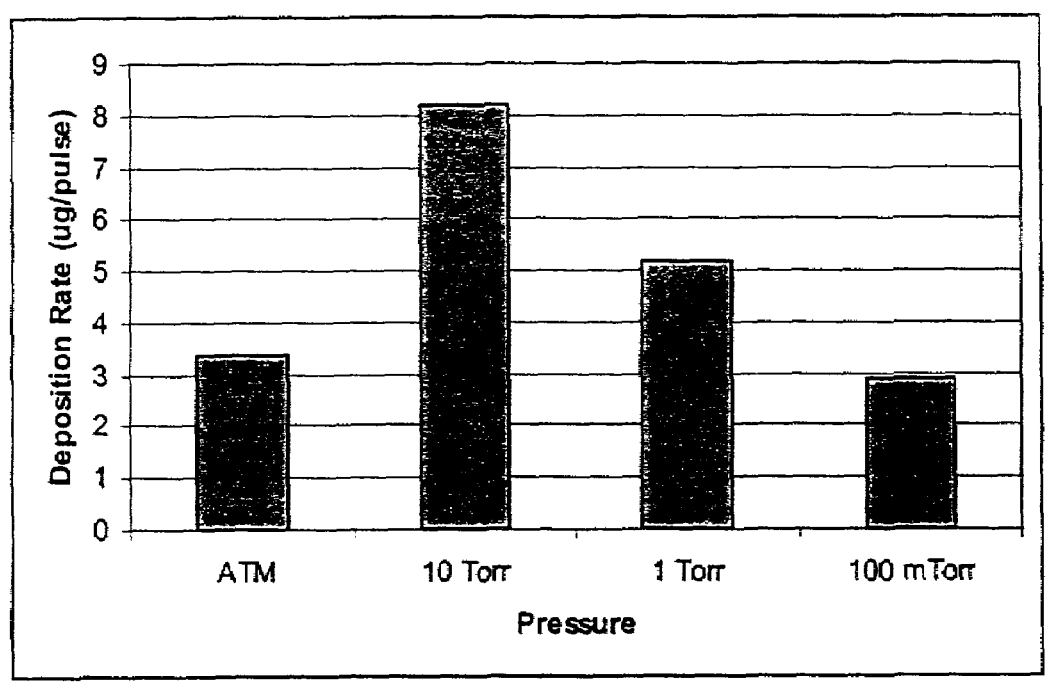
Figure 6    PLGA deposition rate at different pressures.

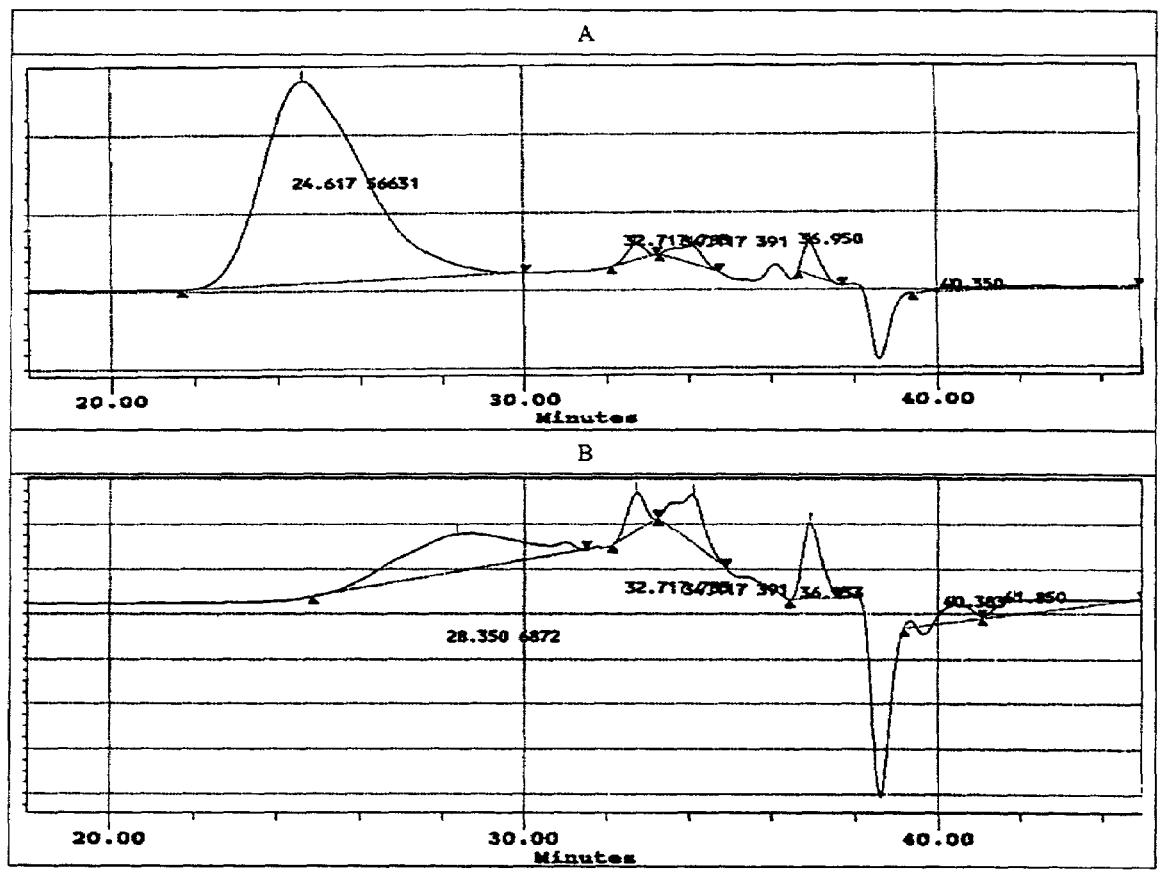
Figure 7    GPC chromatagram of A) original PLGA MW, 56,000 daltons, and B) deposited PLGA at 200 mJ at atmospheric pressure, MW 7,000 daltons.

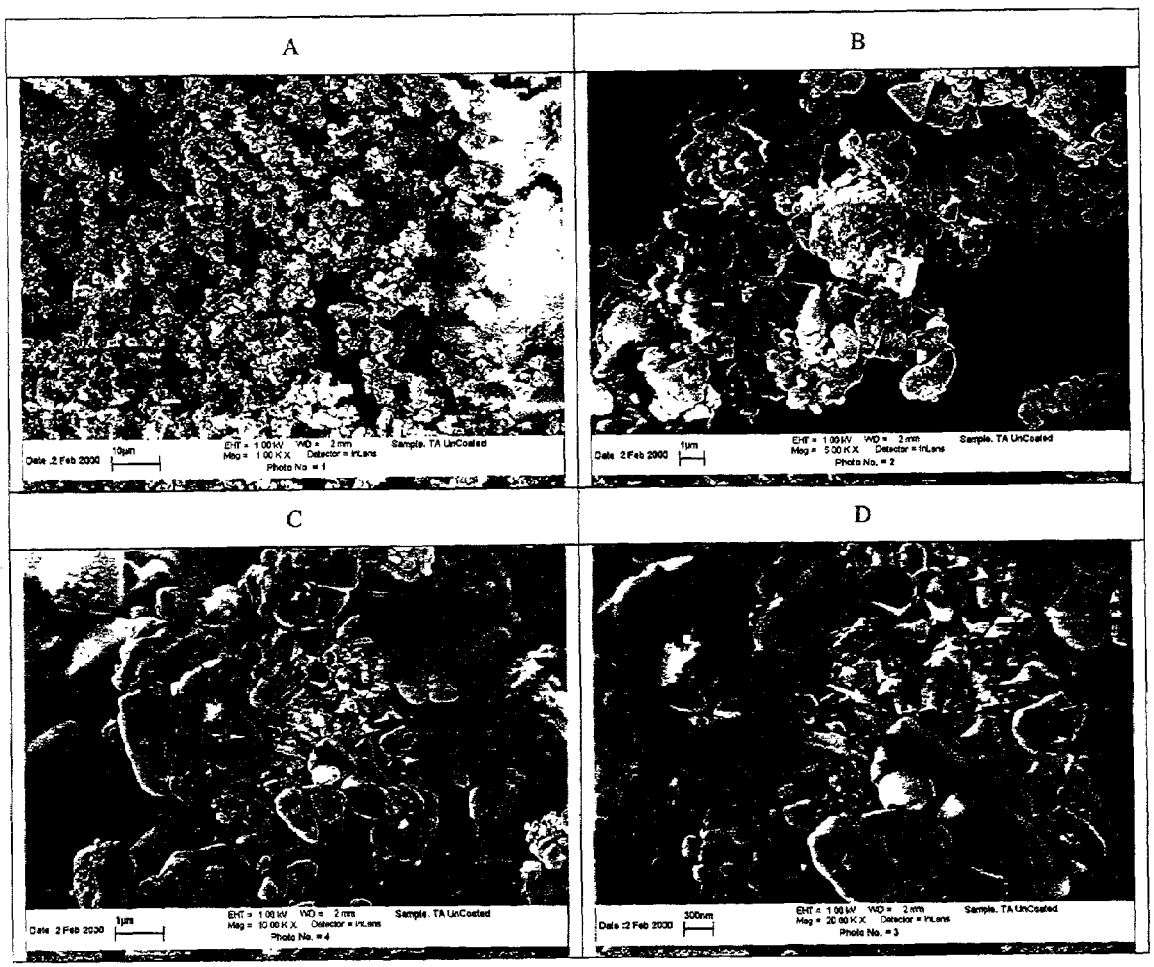
Figure 8    SEM micrographs of uncoated TA powder at A) 1,000, B) 5,000, C) 10,000, and D) 20,000 times magnification.

Figure 9   SEM micrographs of PLGA-coated TA powder at A) 1,000, B) 5,000, C) 10,000, and D) 20,000 times magnification.

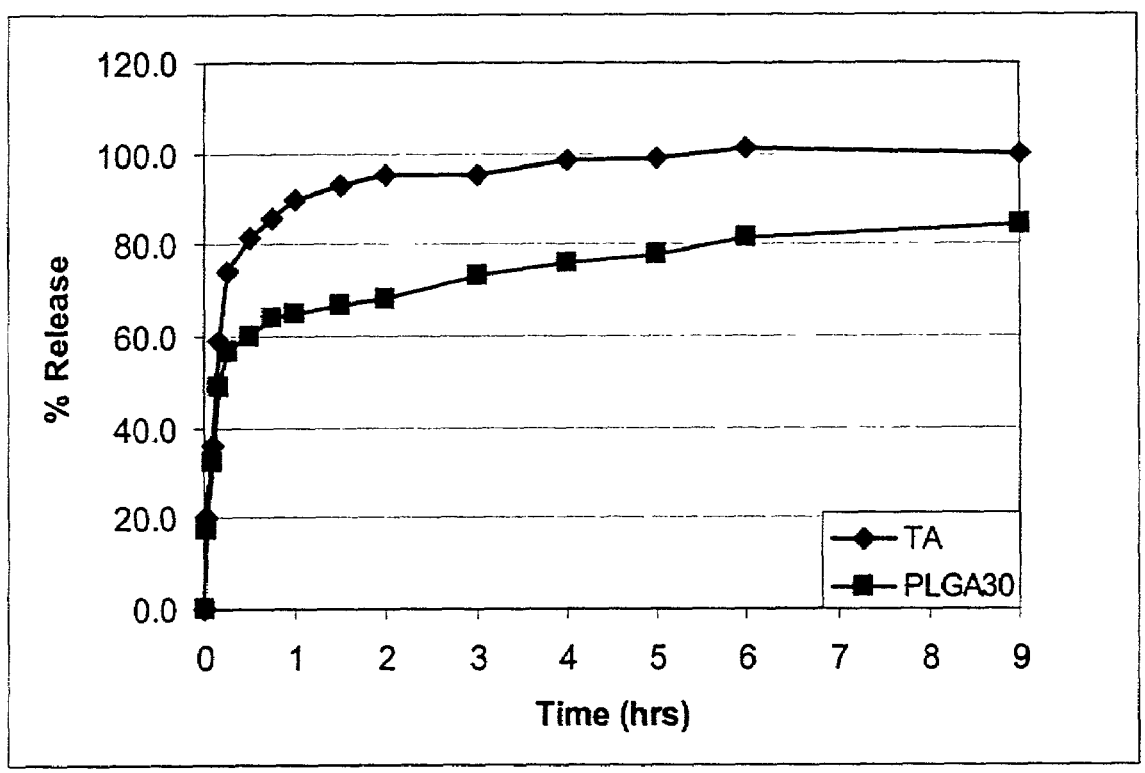
Figure 10: Dissolution of uncoated TA vs. PLGA-coated TA in pH 7.4 PBS (50 mM, 1 % SDS) at 37°C (n=3). Profiles are shown for uncoated TA powder (TA) ♦, and coated powders after 30 minutes at 200 mJ (PLGA30) ■ at atmospheric pressure.

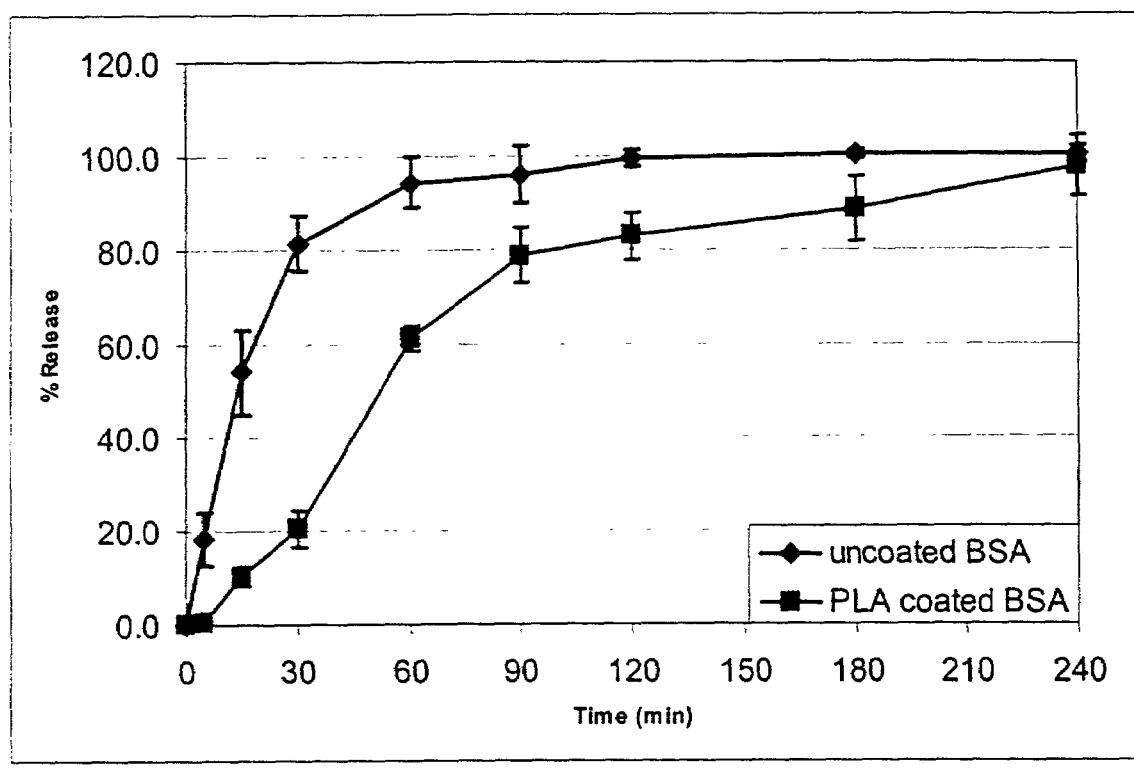
Figure 11: Release profile for PLGA coated BSA.

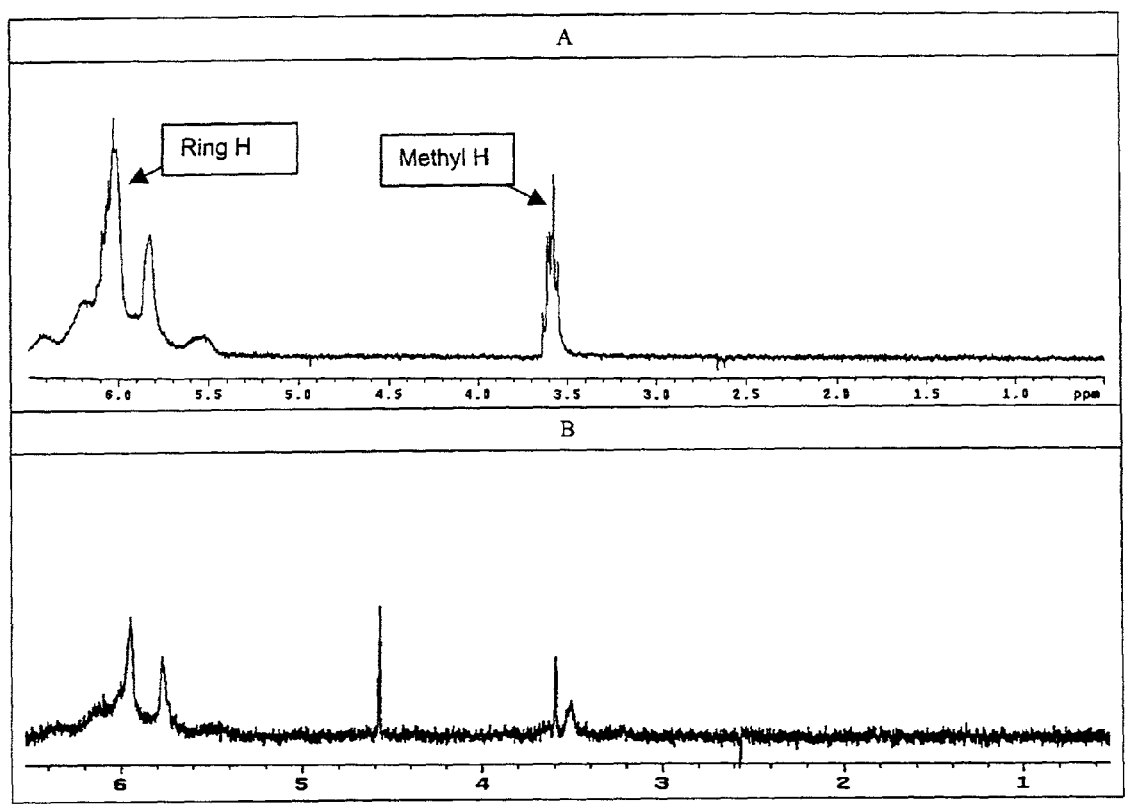
Figure 12   1H-NMR spectra of A) original HPMC, B) deposited HPMC at 200 mJ near atmospheric pressure (10 Torr).

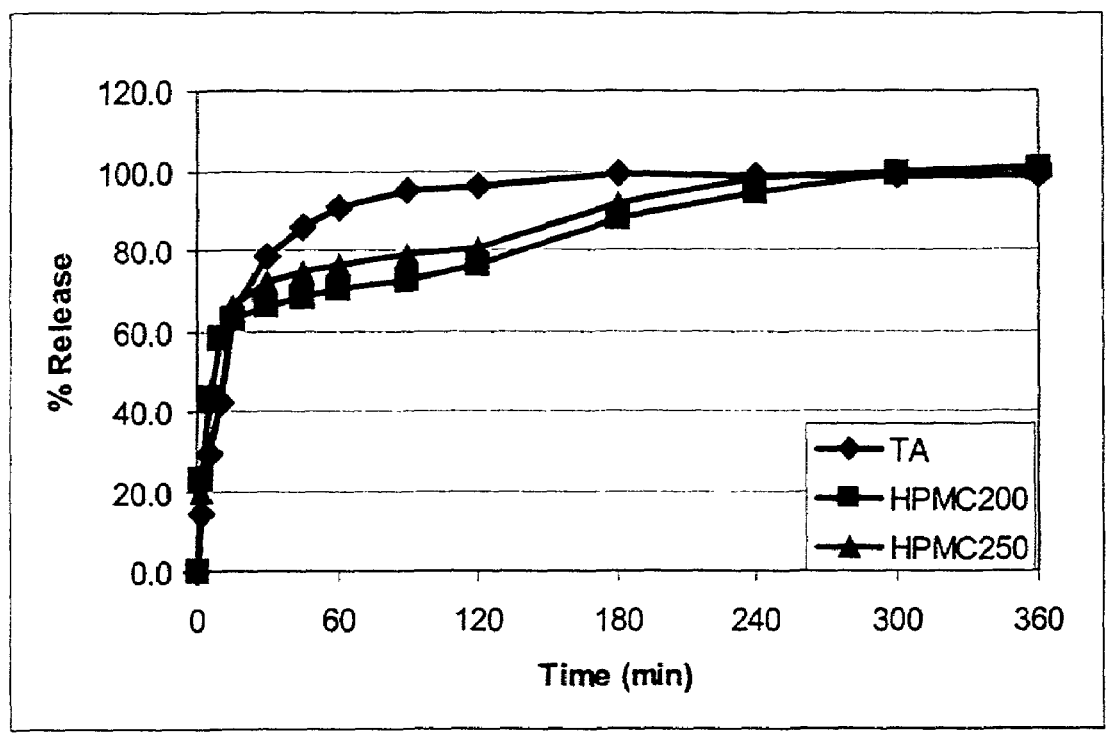
Figure 13: Dissolution of uncoated TA vs. HPMC-coated TA in pH 7.4 PBS (50 mM, 0.5 % SDS) at 37EC (n=3). Profiles are shown for uncoated TA powder (TA) ♦, and coated powders after 10 minutes at 500 mJ/cm$^2$ (HPMC200) ■ and 625 mJ/cm2 (HPMC250) ▲.

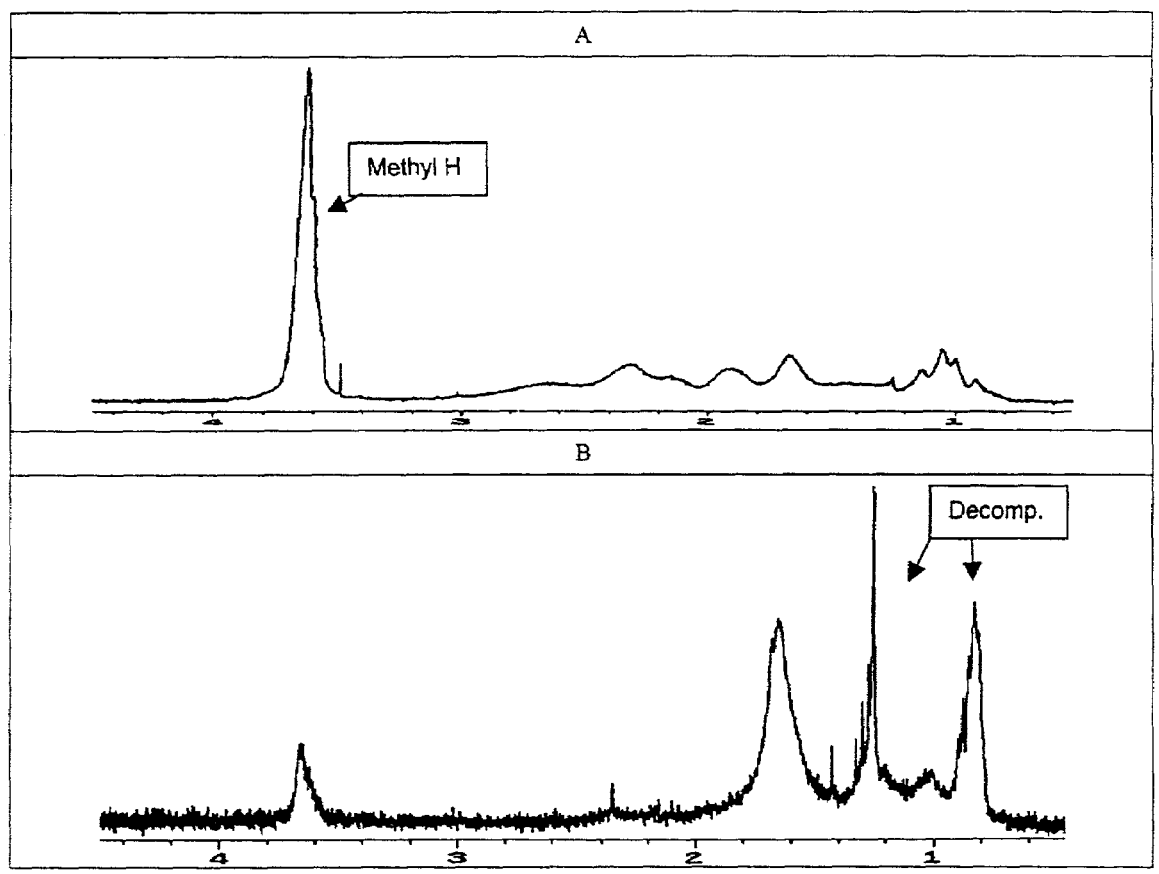
Figure 14  1H-NMR spectra of A) original Eudragit 4135, B) deposited Eudragit at 200 mJ near atmospheric pressure (10 Torr).

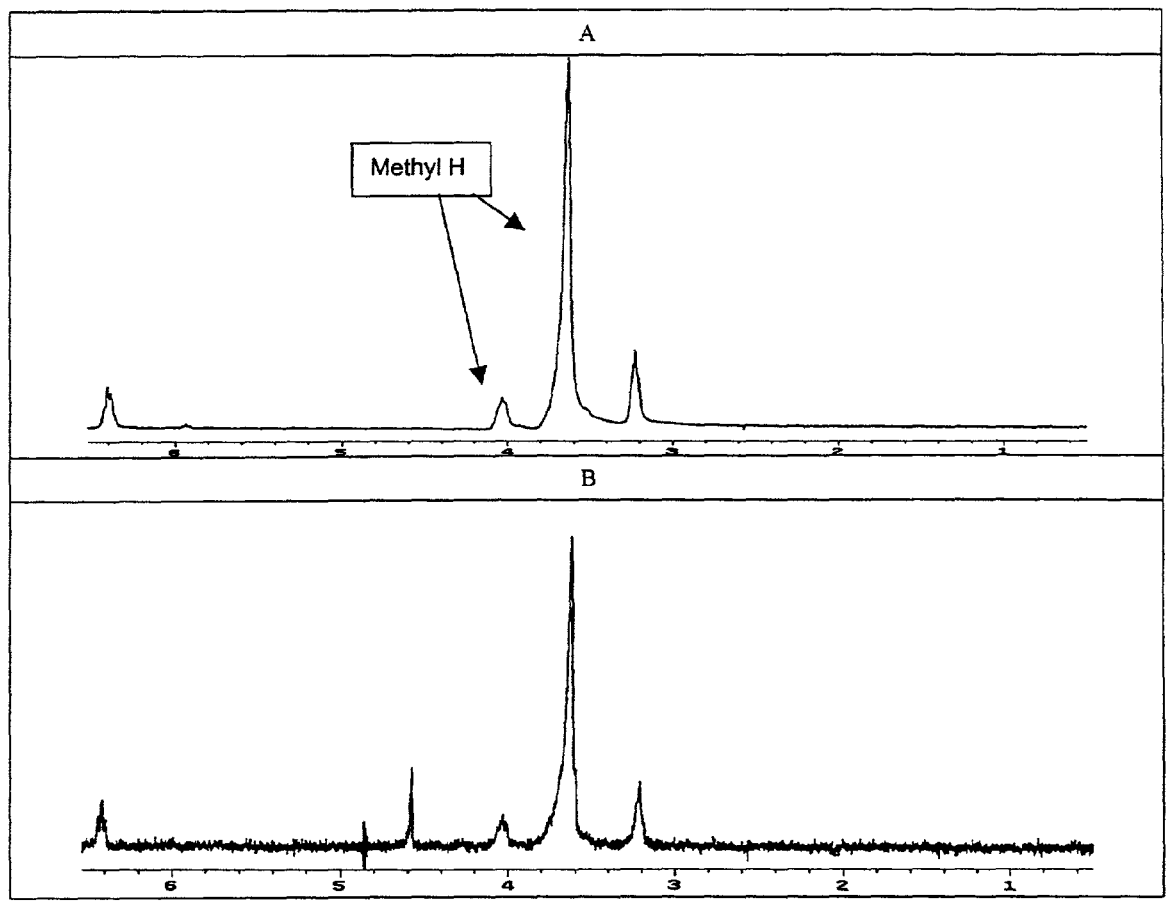
Figure 15  1H-NMR spectra of A) original SDS, B) deposited SDS at 200 mJ near atmospheric pressure (10 Torr).

Figure 16     Anderson Cascade impaction profile for uncoated vs. SDS-coated TA powders.

METHODS FOR COATING PARTICLES AND PARTICLES PRODUCED THEREBY

A. RELATED APPLICATIONS

The present application is a continuation of Ser. No. 09/588,208 filed Jun. 6, 2000, now U.S. Pat. No. 6,406,745, and claims priority under 35 U.S.C. § 119 to U.S. Provisional Patent Application Ser. No. 60/137,733, filed Jun. 7, 1999, and No. 60/138,006, filed Jun. 7, 1999. The entire contents of each of the aforementioned applications is specifically incorporated herein by reference in its entirety.

II. BACKGROUND OF THE INVENTION

B. Field of the Invention

The invention relates to methods of coating particles, and the particles produced thereby. More specifically, the invention relates to drug particles or drug delivery particles coated with a material, which may be biodegradable or biocompatible, such as a polymer. The coating may impart a number of characteristics to the particle including altering its surface properties, its rate of dissolution, or its rate of diffusion and/or release of an active component. More particularly, the invention provides methods for preparing particulate compositions that are coated with ultrafine layers of coating materials, preferably organic polymeric coating materials, applied through a non-aqueous, non-solvent technique. A particularly preferred process is a vapor deposition process such as pulsed laser ablation. Among the many advantages of the disclosed methods are control of both the thickness and uniformity of the coating on the surfaces of the selected particulate drug.

C. Description of Related Art

Pharmaceutical formulations that provide for delivery of a drug over an extended period of time have revolutionized the pharmaceutical industry. Whether the delivery is sustained, modified, controlled, extended, or delayed, the concept is generally the same—provide in a single dose what previously required multiple doses. ("Sustained release" will be used herein to describe this generic class of release mechanisms.) The desire is to provide an effective concentration of the drug for an appropriate length of time.

There are several advantages to such formulations. For example, having a lower concentration of the drug in the body for a longer period of time lowers the incidence of toxicity for drugs with a narrow therapeutic window, and often improves the overall effect. Also, patient compliance is improved when the dosing regimen is decreased; a patient is far more likely to take a single daily dose, than to take two, three, or even four doses daily. This is true for drugs delivered orally, as well as those which are injected, inhaled, or delivered by transdermal or transmucosal diffusion.

Traditionally, sustained release has been achieved by placing a coating material over the drug particles or granules. Thus, tablets, capsules, caplets, pills, and other formulations with coated granules have been provided. Depending on the desired drug release properties, a drug core may be coated with a single layer of coating, or alternating coatings may be provided, or the drug may actually be interdispersed within a coating material. The possibilities are numerous, and the particulars of the formulation are chosen based on the desired drug release properties. A summary of such formulations is provided in *Modern Pharmaceutics*, Second Edition, edited by Gilbert S. Banker and Christopher T Rhodes, the entire contents of which is hereby incorporated by reference.

Oral and other sustained release deliver; systems have largely been based on solvent-based particulate or matrix-type systems. These systems utilize spray-coating or mechanical mixing of a core drug particle and/or excipient granule with a polymer, e.g., a cellulose, polyacrylate, degradable polyester, etc., to control the rate of release of the active drug substance. In addition, traditional matrix systems may contain a gel-forming excipient, e.g., polyvinyl alcohol (PVA), polyethylene oxide (or polyethylene glycol, PEG), celluloses, etc., that form a gel layer after delivery that releases the drug over time by diffusion of the drug through the matrix. A limitation of these systems is that multi-stage scale-up from the laboratory to commercial-scale production of formulations can be lengthy and difficult, often requiring specialized equipment and expensive solvents. Additionally, known systems produce formulations that have a relatively high concentration of polymer, thick coatings, and tend not to be reproducibly manufactured with identical release profiles.

Therefore, what is needed are improved methods for preparing coated drug particles that do not suffer these limitations, and that are useful in preparing pharmaceutical formulations with superior drug delivery and efficacy properties.

III. SUMMARY OF THE INVENTION

A. Features and Advantages of the Invention

The present invention overcomes these and other inherent deficiencies in the prior art by providing novel coating methods for use in preparing coated particles, and in particular, coated drug particles for having improved pharmaceutical properties. In general, the methods disclosed herein provide a means for coating particulate materials with one or more layers of discrete coating matter or materials such that the coated matter or materials adheres generally uniformly to the surface of the particulate materials to form either continuous or discontinuous coatings depending upon the particular application of the coated particulate materials.

The invention also provides for modification of (1) the aggregation characteristics; (2) the flow properties; and (3) the release-rate of the drug, by applying coatings using the methods of the present invention to greatly enhance the pharmacokinetic profiles of coated drugs.

Additional advantages include improved flow properties during manufacture; and formulation stability, e.g., shelf-life.

Drugs coated by the processes outlined herein have been shown to possess high encapsulation efficiencies (>99% drug) while requiring minimal processing. The process also has several advantages over current coating techniques including:

1. It is a fast process with modification times (i.e., how long it takes to coat a particulate from beginning to end) on the order of minutes.

2. A variety of materials can be used for producing the coatings on the particulate materials, thus it is possible to produce films from materials with proven biocompatibility.

3. It can be a dry, solventless technique conducted under a sterile environment, which is an important consideration in the drug industry.

4. Particle agglomeration/adhesion can be minimized by applying coatings that affect the bonding nature and electrostatic charge on the surface of the particulate materials.

5. Formation of microcapsules by depositing coatings onto the particle surface will make it possible to control drug release kinetics by: (a) diffusion of the drug through the polymer; (b) degradation of the biodegradable polymer coating off of the drug particles, thereby releasing the core drug material.

6. Laser ablation can be performed under normal atmospheric pressure, as opposed to a vacuum, thereby eliminating the need for vacuum mechanisms, including chambers and pumps, in the process, and allowing for a continuous production line. This advantage significantly improves production times, and thereby decreasing production costs and scale-up difficulty.

B. SUMMARY OF THE INVENTION

The present invention provides methods of coating core materials comprising: providing target materials and core materials: ablating the target materials to form ablated particulate target materials: and coating the core materials with the ablated particulate target materials; wherein the method occurs at a pressure of about 10 Torr or higher. The ablating may occur at a pressure of about 20 Torr or higher, including about 760 Torr.

The core materials may have an average diameter of about 0.5 μm to about 1 mm. Coating the core materials with the ablated particulate target material may result in a coating of the target materials on the core materials of a thickness of less than about 1000 nm. The coating on the core materials may have a thickness of less than about 100 nm, or less than about 10 nm.

Coating the core materials with the ablated particulate target materials may result in coated particles having average diameters of less than about 1 mm, less than about 100 μm, or less than about 10 μm. Preferably, the target materials include at least a biodegradable polymer, biocompatible polymer, polysaccharide, and/or protein.

Ablating may be achieved by the use of a high energy source, which may be a laser. Lasers include, but are not limited to, ion laser, diode array laser, and pulsed excimer laser. In preferred embodiments, the coating of the core materials with the ablated particulate target materials is performed by mixing the core materials with the ablated particulate materials using fluidization. The fluidization may be achieved by pneumatic fluidization.

The core materials may include pharmaceuticals for human or animal use, pesticides, herbicides, fungicides, cosmetics, paints or pigments, and/or inert particles. Preferably, the core materials includes at least one pharmaceutical for human or animal use. The coating of the target materials on the core materials may result in a continuous coating or a discontinuous coating.

In other embodiments, the present invention includes methods of coating particulates to a coating thickness of less than about 100 nm, the method comprising: providing target materials and core materials; ablating the target materials to form ablated particulate target materials; and coating the core materials with the ablated particulate target materials; wherein the core materials are fluidized using pneumatic fluidization.

In other embodiments, the invention includes methods of coating core materials comprising: providing target materials and core materials; ablating the target materials to form ablated particulate target materials; and coating the core materials with the ablated particulate target materials; wherein the method occurs at a pressure of about 760 Torr and wherein the core material is fluidized using pneumatic fluidization.

The present invention also provides coated particulates formed according to these methods.

IV. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 3 shows a TEM image of deposited nanoparticles film at atmospheric pressure (scale 100,000 times).

FIG. 4 shows another TEM image of deposited nanoparticles film at atmospheric pressure (scale 100,000 times).

FIG. 5 shows a 1H-NMR spectra of A) original PLGA, B) deposited PLGA at 500 $mJ/cm^2$ at atmospheric pressure, and C) near atmospheric pressure (10 Torr).

FIG. 6 shows the PLGA deposition rate at different pressures.

FIG. 7 shows a gel permeation chromatogram of A) original PLGA MW, 56,000 daltons, and B) deposited PLGA at 500 $mJ/cm^2$ at atmospheric pressure, MW 7,000 daltons.

FIG. 8 shows SEM micrographs of uncoated TA powder at A) 1,000, B) 5,000, C) 10,000, and D) 20,000 times magnification.

FIG. 9 shows SEM micrographs of PLGA-coated TA powder at A) 1,000, B) 5,000, C) 10,000, and D) 20,000 times magnification.

FIG. 10 shows dissolution of uncoated TA vs. PLGA-coated TA in pH 7.4 PBS (50 mM, 1% SDS) at 37° C. (n=3). Profiles are shown for uncoated TA powder (TA)♦, and coated powders after 30 minutes at 500 $mJ/cm^2$ (PLGA30)■ at atmospheric pressure.

FIG. 11 shows the release profile for PLGA coated BSA ■ compared to uncoated BSA ♦.

FIG. 12 shows a 1H-NMR spectra of A) original HPMC, B) deposited HPMC at 500 $mJ/cm^2$ near atmospheric pressure (10 Torr).

FIG. 13 shows the dissolution of uncoated TA vs. HPMC-coated TA in pH 7.4 PBS (50 mM, 0.5% SDS) at 37° C. (n=3). Profiles are shown for uncoated TA powder (TA) ♦, and coated powders after 10 minutes at 500 $mJ/cm^2$ (HPMC200) ■ and 625 mJ/cm2 (HPMC250) ▲.

FIG. 14 shows a 1H-NMR spectra of A) original Eudragit 4135, B) deposited Eudragit at 500 $mJ/cm^2$ near atmospheric pressure (10 Torr).

FIG. 15 shows a 1H-NMR spectra of A) original SDS, B) deposited SDS at 500 $mJ/cm^2$ near atmospheric pressure (10 Torr).

FIG. 16 shows an Anderson Cascade impaction profile for uncoated vs. SDS-coated TA powders.

Figure 17:
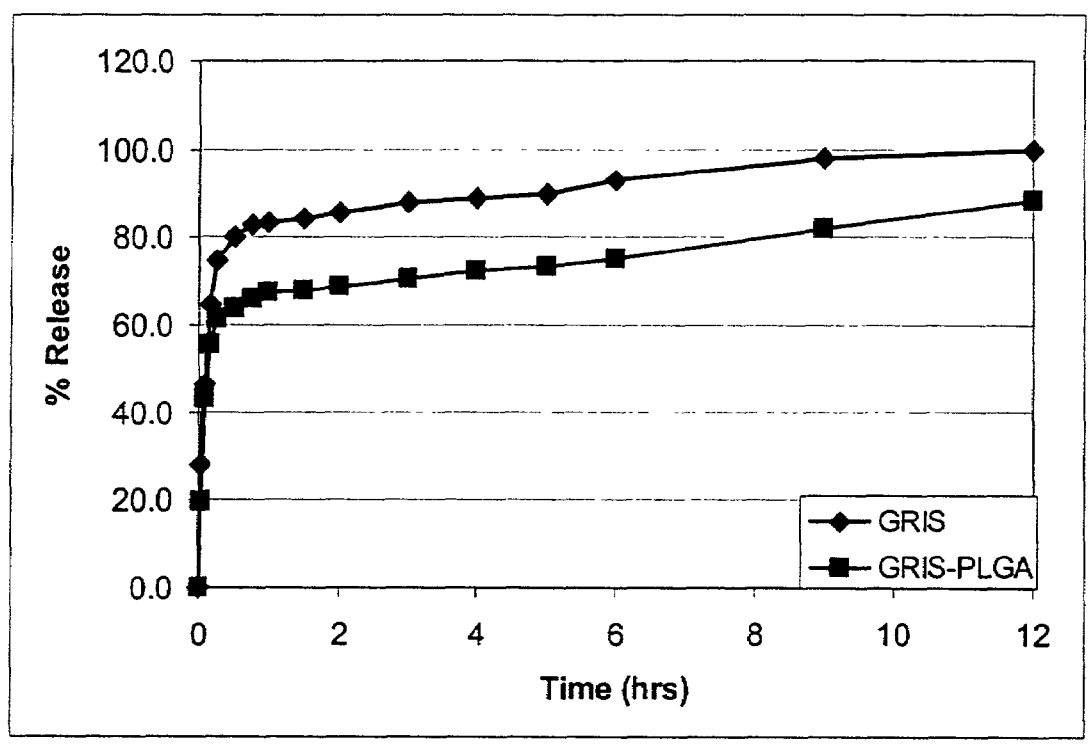

FIG. 17 shows the release profile for PLGA coated Griseofulvin (GRIS) ■ compared to uncoated GRIS ♦.

Figure 18:
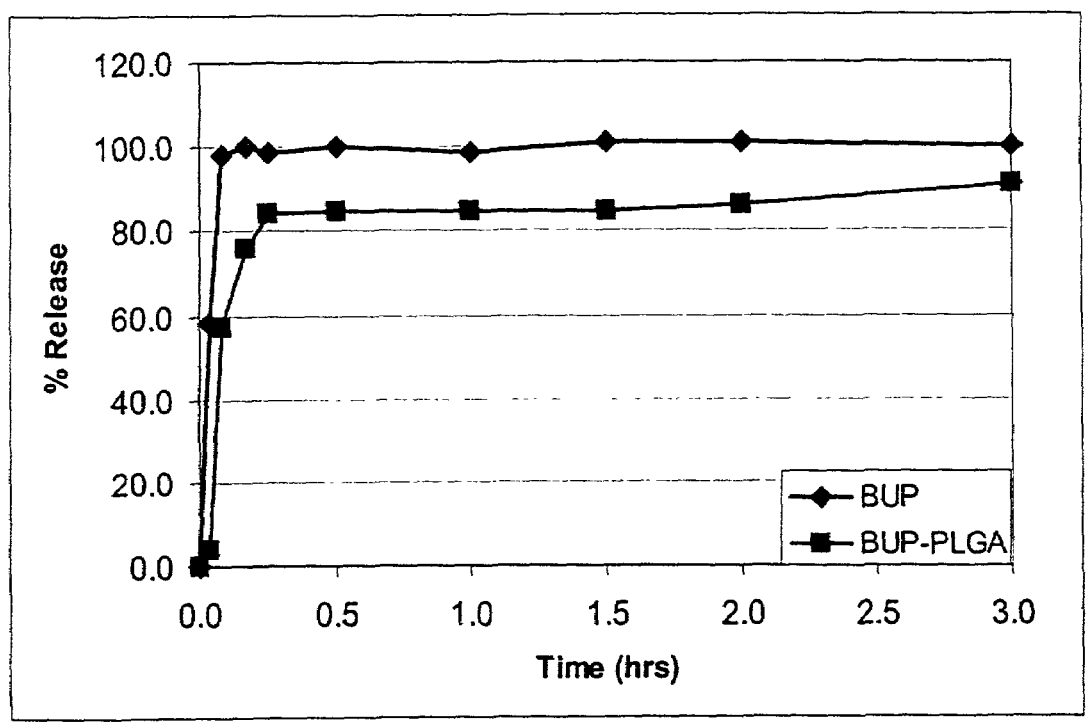

FIG. 18 shows the release profile for PLGA coated Bupivacaine-HCl (BUP) ■ compared to uncoated BUP ♦.

FIG. 19 shows a 1H-NMR spectra of A) original PC, B) original PEG20K, and C) PC+PEG20K solid target deposited at atmospheric pressure.

FIG. 20 shows a 1H-NMR spectra of A) original PC, B) original PEG400, and C) PC+PEG400 liquid target deposited at atmospheric pressure.

FIG. 21 shows a 1H-NMR spectra of A) original PC, B) original PEG20K, and C) PC+PEG20K gel target (heat mixed) deposited at atmospheric pressure.

Figure 22:
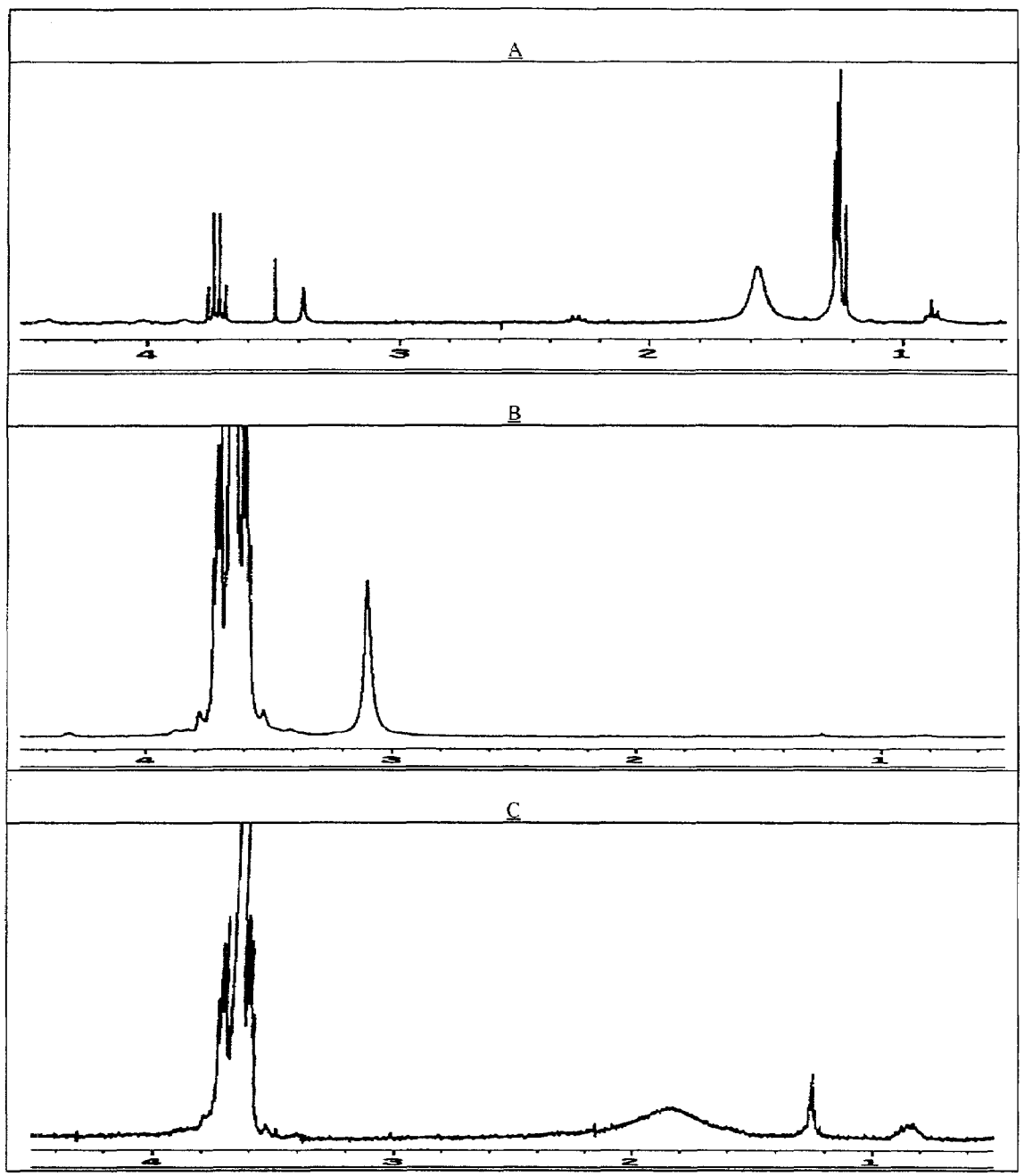

FIG. 22 shows a 1H-NMR spectra of A) original PC, B) original PEG400, and C) PC+PEG400 frozen liquid target deposited at atmospheric pressure.

V. DETAILED DESCRIPTION OF THE INVENTION

The invention is directed to methods of coating particulate materials, and the coated particulate materials produced thereby. Particulates to be coated in accordance with this invention are those in which a thin coating is desirable. Such particulates (cores) include, but are not limited to, drugs or pharmaceuticals for human or animal use, cosmetics, pesticides, herbicides, fungicides, paints and pigments, as well as inert particles for which a thin coating is desirable. Of course, this invention is also applicable to the application of thin layers of active materials to inert particles. Examples might include nanoparticles having biologically active coatings, such as antigens, nucleic acids, proteins, or even pharmaceuticals. The possibilities and combinations are numerous.

The invention is particularly directed to particulate materials in the form of drug or drug delivery materials coated with a material, which may be a biodegradable or biocompatible matter, including biodegradable or biocompatible polymers. The coating may impart a number of characteristics to the particulate material, including altering its surface properties, its rate of dissolution, or its rate of diffusion and/or release of an active component. More particularly, the invention provides methods for preparing particulate material compositions that are coated with ultrafine layers of coating materials, preferably organic polymeric coating materials, preferably applied through a non-aqueous, non-solvent technique. A particularly preferred process is a vapor deposition process using pulsed laser ablation. Among the many advantages of the disclosed methods are control of both the thickness and uniformity of the coating on the surfaces of the selected particulate drug.

A. Methods for Preparing Coated Drug Particles

The method of the present invention generally involves physical vapor deposition (PVD) of the polymer coating onto the surface of the target particulate material. Techniques for achieving PVD are well-known in the art, and include such methods as thermal evaporation, sputtering, and laser ablation of a target material to produce a flux of coating particulate materials, which are then contacted with the core particulate material, and allowed to form a coating thereon. A most preferred method is laser ablation. Depending upon the amount of vapor or the length of deposition, the number of coating particles, and the thickness of the resulting layer of coating onto the core particulate material can be varied to achieve the particular objectives of a given coating process. Laser ablation for coating particles under very low pressure is disclosed in WO 00/28969, the entire contents of which is hereby incorporated by reference.

Throughout this specification, the terms "core material," "core particles," and "core particulate materials" will be used interchangeably, as will the terms "coating material," "coating particles," and "coating particulate materials." These interchangeable terms are intended to have the same meanings as used herein.

In this invention, PLD or pulsed laser ablation is used in the preparation of ultrafine, fine, and granular drugs particles/particulate materials having atomic to nanometric thick coatings that impart improved pharmaceutical properties to the resulting coated drugs. The present coating methods are particularly desirable, since the core drug particles themselves are not subjected to conditions that would decompose, destroy, or alter the activity of the drug itself. The use of PLD also minimizes the thermal decomposition or denaturation of the coating material itself, and permits the deposition of the coating material onto core drug particles that may be maintained at ambient temperature and atmospheric pressure during the deposition process.

Through regulation of the physical parameters of the deposition process (including background gas and pressure and coating exposure time) the skilled artisan may now for the first time prepare a variety of particulate drugs that comprise ultrafine particulate coatings. In particular, the method affords the control of both the extent of molecular coating, and the thickness of the resulting coating layer on the surfaces of the drug particles. Both relatively thick coating layers, and relatively thin coating layers may be produced by controlling the extent of laser ablation process and the exposure of the coating particles to the laser ablated coating material.

By choosing a correct energy density, the target material for coating ablates in a cluster-like form that retains a majority of the characteristics of the target material. Generally, when the energy density (fluence) is increased, the ablation has more of an atomic character, and is composed of atoms that do not resemble the signature of the original material.

To provide optimum deposition of the coating onto the surface of the core particle, fluidization or agitation mechanisms may be employed to agitate the core particles during the coating process both to prevent agglomeration of the resulting coated core particles, and also to control the extent of coating thickness onto the core particles. Such mechanisms may involve subjecting the target particles to a stream of air or gas or other fluid to agitate the particles during the vapor deposition process, or alternatively may involve physical stirring. Some applications may require the use of both mechanical stirring and pneumatic fluidization to achieve the intended results. The present method provides an improvement for producing individual coated particles that remain essentially or substantially non-agglomerated after coating.

Operating the coating process at approximate atmospheric pressure allows for a continuous production process. Rather than needing to apply a vacuum on each batch for coating, the process of the present invention, operated at near atmospheric pressure, allows for continuous processing. For example, uncoated particles are transported into a fluidized bed coating chamber and coated using the present method, at atmospheric pressure. The continuous fluidizing mechanism, e.g., a gas stream, is sufficient to lift only the uncoated particles into the coating chamber. As the coating is applied, the particles become heavier, and fall out of the gas stream, to be transported out of the chamber. As an alternative, a circular gas flow (cyclone) may be applied to simultaneously separate and coat particles in a continuous fashion. This process continues as more uncoated particles are transported in, and coated particles are transported out. In addition, mechanical agitation may be included from the bottom to improve the fluidization at lower gas flow rates. A relatively inert atmosphere is maintained by constantly flowing a gas such as helium into the chamber. The gas may be recycled after filtering and scrubbing. Preferably the gas to be used is relatively light and inert. Preferable gases helium, argon, nitrogen, etc. Alternatively, if desired, a more reactive gas may be included, or used alone.

The invention is operated such that the coating chamber has a pressure of around atmospheric pressure, which may be a pressure as low as about 10 Torr to as high as about 2500, or any pressure in between. Preferably, the pressure in the coating chamber is greater than about 20, or 30, or 40, or 50 Torr, more preferably greater than about 100 or 500 Torr, and most preferably greater than about 700 Torr. Preferably, the pressure in the coating chamber is less than about 1000, more preferably less than about 900, and most preferably less than about 820. In a most preferred embodiment, the pressure in the coating chamber is about 760 Torr, or atmospheric pressure.

The materials employed in the coating process are preferably materials such that when ablated by an energy source, comprise a vapor of discrete particles that are extremely small—typically preferred are coating particles that are sized on the order of from about 1 to about 1000 nanometers in average diameter. It should be recognized that the particles discussed in this application are not necessarily spherical, but may be irregularly shaped. Thus, reference to diameter is meant to include an "equivalent diameter," or "geometric equivalent diameter," recognizing that particles may be irregular. This measurement may be determined by light scattering measurements, such as by using a Coulter Counter (Beckman Coulter, Inc. Fullerton, Calif.). Techniques for measuring irregularly shaped particles are discussed in Small Particle Statistics, the entire contents of which is hereby incorporated by reference.

The deposition materials employed in the preparation of coated drug particles may comprise an inorganic or an organic material, including but not limited to, polymers, proteins, sugars, lipids, as well as bioactive ceramics, anionic, cationic, or zwitterionic polymers or lipids, and also antibodies or antigens. In preferred embodiments an organic polymer is selected for laser ablation and deposition onto the surface of pharmaceutical compounds. Particularly preferred as coating materials are organic compounds such as PLA, PGA, PLGA, and related biodegradable polymers, and functionalized derivatives thereof.

The materials applied as coatings may act to modify the release rate or cell uptake of an active compound in the particle core. Such sustained-release coatings generally will act through diffusion or dissolution modification mechanisms.

The coatings may also act to improve the physical stability of the drug particle, so as to improve, for example, its resistance to chipping or cracking. A coating may also serve as a moisture barrier, improving shelf-life of an otherwise rapidly degrading drug. Because of the potential for dry coating pharmaceutical particulates, use of the present invention is especially advantageous for coating to improve shelf-life. Thus, the present invention is especially applicable for coating pharmaceutical formulations which are sensitive to moisture, or solvents (such as proteins), and are therefore difficult to coat. This invention solves that problem. Moreover, the quality of the coating of the present invention, i.e., its potential to be non-porous, is unique and provides one more advantage for coating sensitive compounds.

A unique aspect of this invention is its ability to produce coatings that are substantially non-porous. Solvent-based coating techniques produce porous coatings because, during drying, the solvent evaporates, leaving minute pores in the coating. Because pores are formed during the coating, more coating is required to obtain a proper seal. Thus, a thicker coating is required when solvent-based techniques are used. This invention, on the other hand, allows for extremely thin coatings, at least in part because of their integrity—they are almost completely non-porous, because applying a coating from nanometric-scale particles, the relative thickness may still be on the order of 10 to 50 nm.

The coating may also play a direct role in the pharmacology, or pharmacokinetics, of the pharmaceutical particle. For example, the coating may modify the interaction of the particle with tissues or cells, targeting specific cell or tissue types, or improving cell uptake, or even acting to provoke an immune response. The methods of the present invention may even be used to coat nucleic acids to inert particles with the purpose of particle bombardment transfection of plants or animals (for use in a "gene gun"). The possibilities are too numerous to list here. In short, this invention provides improved methods for coating particles for all known coated particle applications, and for applications which are disclosed herein for the first time.

These materials may be readily deposited onto the surface of drug particles in preferred particle sizes and layer thicknesses using the laser ablation apparatus and method disclosed herein. This method may be used to deposit one or more layers of nanometric-sized coating (each on the order of from about 1 nm to about 1000 or so nm in thickness) on core particles that range on the order of from about 0.1 μm to about 1 mm in diameter. The average size of the resulting coated drug particles may range from about 0.1 μm to as high as several millimeters or so in diameter. Obviously, the size of the coated particle will depend on the needs of the user, with smaller coated particles finding application in, for example, in molecular biology applications, and larger coated particles finding application in, for example, pharmaceutical formulations.

The core particulate material to be coated in the process are preferably gas and/or mechanically fluidized to improve coating uniformity during deposition. By controlling conditions during deposition, the coating thickness, particle size, and adhesion can be varied.

This coating method provides rapid thermal evaporation from the pulsed excimer laser to coat solid materials onto particles. Through this method, the coating material is generally less than about 1 to 5% by mass, and coating times are under one hour without the need for drying solvents. This method has a wide variety of pharmaceutical applications ranging from coatings to improve agglomeration and flowability, stability, cell uptake and interactions, as well as controlling the release rate of the drug.

Drug particles or drug delivery particles coated with biodegradable or biocompatible polymer coatings with controlled thickness and controlled coating uniformity may be produced using the apparatus and methods as described herein. The drug particle coating thickness can be controlled down to nanometer thicknesses, and encapsulation can be partial or complete.

Core particulate material, which may range in size, for example, from several nanometers to several millimeters in diameter, is provided with a relatively uniformly dispersed discontinuous or continuous coating of discrete individual coating particles sized from atomic scale to a few nanometers. The coating particles are created by a vapor deposition process, and preferably by laser ablation, where a pulsed laser beam is aimed at a target composed of the coating material under conditions sufficient to release individual particles from the target in a generally perpendicular ablation flux, e.g., a solid target material, frozen liquid matrix target, etc. Pulsed laser ablation is especially suited for multi-elemental deposition in which the stoichiometry of the ablated species is maintained. This may be important when organic coating materials, such as polymers or other mesoscopic entities such as antibodies, are employed (Agarwal, 1998). During laser ablation, the core particulate material may be agitated or fluidized such that there is relatively continuous movement between all the core particles. The degree of coating is controlled by varying the laser parameters, energy density and number of pulses, and the treatment time.

Coated drug particles and pharmaceuticals may be prepared with a uniform coating. Such a coating may delay drug diffusion and dissolution until the coating degrades or until the drug diffuses through the coating for non-degradable coatings. The uniform coating may also be used to protect the drug particle from hostile environments. A coating may control the release rate by affecting surface area. The coating may also protect the drug particle size during processing steps such as compacted tablet grinding by providing a weaker interface that separates before the stresses fracture the drug particles themselves. The coating may also improve flow characteristics, which can be significant during manufacturing or in determining the efficiency of drug delivery mechanisms.

B. Apparatus for Coating Particulates

The apparatus of the invention generally includes a coating chamber in which a target material and particulate substrate is placed. An external evaporation or removal source (EORS), such as a pulsed excimer laser, enters the chamber through a window, preferably quartz, and interacts with the matrix target (MT). In alternative embodiments, the evaporation or removal source is internal, i.e., in the same chamber as the matrix and particles.

A nanometer-thin layer of target material absorbs the energy from the laser pulse and the surface is rapidly heated and expands from the target in the form of a plume of ablated atomic to micrometer sized particles. The plume of particles is then deposited onto the fluidized core particles.

A region of target absorbs the incident energy, for example, an excimer laser (UV excimer laser at 193–308 nm, solid-state Nd-Yag lasers at 255 to 1064 nm, etc.). The absorption depth of the incident laser depends on the structure of the biocompatible target, typically the absorption depth will range from 10–100 nanometers. This rapid (nanoseconds) absorption and subsequent heating of the target surface by the laser pulse provides energy for polymer desorption from the biocompatible target. Due to differential changes in the heated target in a time regime of nanoseconds, the matrix target ablates from the surface into a dense plume of nanometric-sized clusters, molecules, molecular chains, polymers, and/or lipid fragments, for example. (For a discussion of laser ablation of polymer, see Ogale, 1994, incorporated herein by reference.) The plume of nanometric-sized clusters, molecules, molecular chains, polymers, and lipid fragments, and particles are then deposited onto the fluidized core particles. (For a discussion of fluidization, see Kodas and Hampden-Smith, 1999, incorporated herein by reference.)

The MT preferably includes a matrix of biocompatible or biodegradable coating material and/or mesoscopic molecules that modify surface interactions. Biocompatible coating materials used for the MT may include polymers, proteins, sugars, lipids, and/or other biologically active or inactive materials. Nanofunctional molecules that modify the surface interactions may include bioactive ceramics, anionic or cationic polymers and lipids, antibodies, or antigens. The MT, in solid, liquid, or gel form, may alternatively be dispersed in a solvent that evaporates relatively quickly from the core particles. The core particles may be pharmaceutically relevant particles such as an active drug, pharmaceutically inert excipient particles, or other preformed particulate mixtures.

The core particles, or particulate materials, are preferably fluidized within the coating chamber to improve the uniformity of coating. The fluidization is preferably achieved by air/gas stream fluidization. That is, the core particles or core particulate materials are placed in the path of flowing air or gas, which fluidizes the cores, improving their mixing and exposure to the coating chamber atmosphere. Fluidization may also be achieved by mechanical mixing, but air/gas fluidization is preferable. Hybrid air/gas/mechanical fluidizing mechanisms are also preferable.

Having the EORS (e.g., laser) and the coating chamber separate allows great latitude for varying the coating structure and thickness. Also, with the proper EORS choice, the process can be used to create coatings on many different materials or particulates. The composition of the coatings is strongly dependent on the laser processing parameters such as incident energy fluence ($J/cm^2$), laser repetition frequency, fluidization gas pressure, fluidization gas molecular weight. target to substrate distance, and the optical absorption coefficient of the matrix target and components.

FIG. 1 shows one embodiment of the present invention. The apparatus of FIG. 1 is a top-coating apparatus 1. Top-coating apparatus 1 includes a coating chamber 2, which is formed from a cylindrical portion 5 connected to a conical portion 3. Although the embodiment of FIG. 1 is shown with a cylindrical coating chamber, other shapes may be chosen, depending on the needs of the user or manufacturer, including, for example, square, rectangular, or polygonal.

Conical portion 3 is connected at its tapered end to a gas-permeable porous plate 7, and a gas distributor 9, adjacent to plate 7. At the opposite end of cylindrical portion 5, a filter 11 with cylindrical housing is mounted. An exhaust duct 13 carries gas for recirculation back through a filter assembly 15, through a blower (not shown), a temperature controller 17, then back to gas distributor 9 before re-entering the chamber. Recirculation, filtration, and temperature control of the chamber gas, are preferred aspects of the present invention.

Top-coating apparatus 1 includes an external evaporation or removal source (EORS) 21, which is directed upward into central chamber 2 through window 23 to the matrix target (MT) 25 at approximately a 45° angle. Window 23 is formed from an optically transparent material, which is preferably quartz. The plume 27 leaves MT 25 downward toward the fluidized particles 41 below MT 25. Plume 27 coats onto particles 41 which are contacted.

An external control device 31 and container 33 are used to feed or turn MT 25, which may involve a rotating motor control and/or feeding tube. Container 33 may also include a chiller to freeze material for MT 25.

Particles 41 are fluidized as a whirling layer at controlled temperature, and solvent 43 from MT 25 is dried simultaneously during the coating process. A mechanical vibrator 45 can be used in conjunction with the gas fluidization to prevent particle agglomeration and apply fluidization at lower gas flow regimes.

FIG. 2 shows another embodiment of the invention, a bottom-coating apparatus 101. Apparatus 101 includes a coating chamber 102, which is formed from a cylindrical portion 105 connected to a conical portion 103. Conical portion 103 is connected at its tapered end to a gaspermeable porous plate 107, and a gas distributor 109, adjacent to plate 107. At the opposite end of cylindrical portion 105, a filter 111 with cylindrical housing is mounted. An exhaust duct 113 carries gas for recirculation back through a filter assembly 115, through a blower (not shown), a temperature controller 117, then back to gas distributor 109 before re-entering the chamber.

External to coating chamber 102 is the EORS 121, which is directed downward into coating chamber 102 through window 123 to the MT 125 at approximately a 45° angle. The aerosol plume 127 leaves MT 125 upward toward the fluidized particles 141 above MT 125, which attaches as a partial coating to the surfaces of exposed particles 41.

An external control device 131 and container 133 are used to feed or turn MT 125, which may involve a rotating motor control and/or feeding tube. Container 133 may also include a chiller to freeze material for MT 125.

Particles 141 are fluidized as a whirling layer at controlled temperature, and solvent 143 from MT 125 is dried simultaneously during the coating process. A mechanical vibrator 145 can be used in conjunction with the gas fluidization to prevent particle agglomeration and apply fluidization at lower gas flow regimes.

Figure 1:
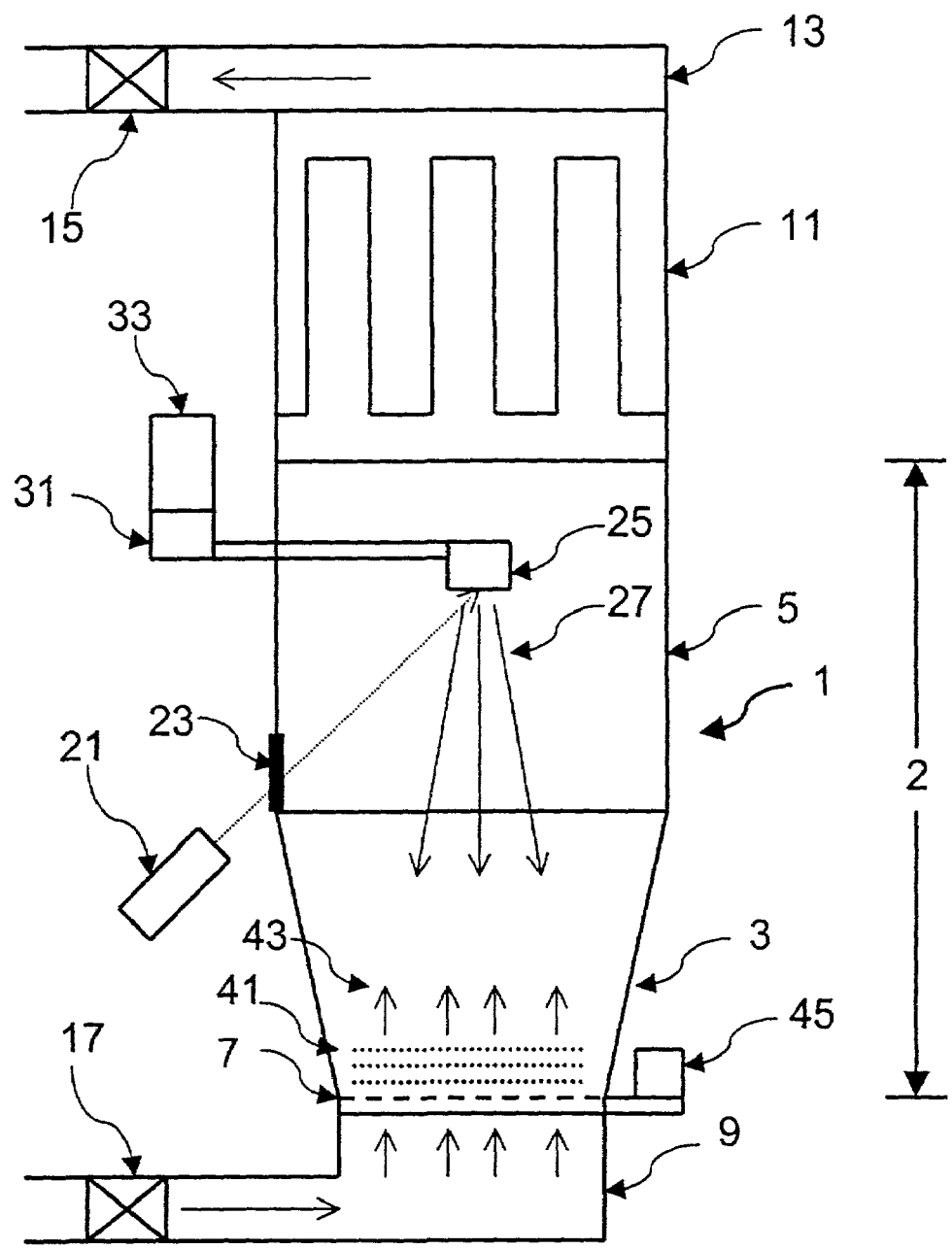
FIG. 1 is a diagrammatic representation of an embodiment of the invention.
Figure 2:
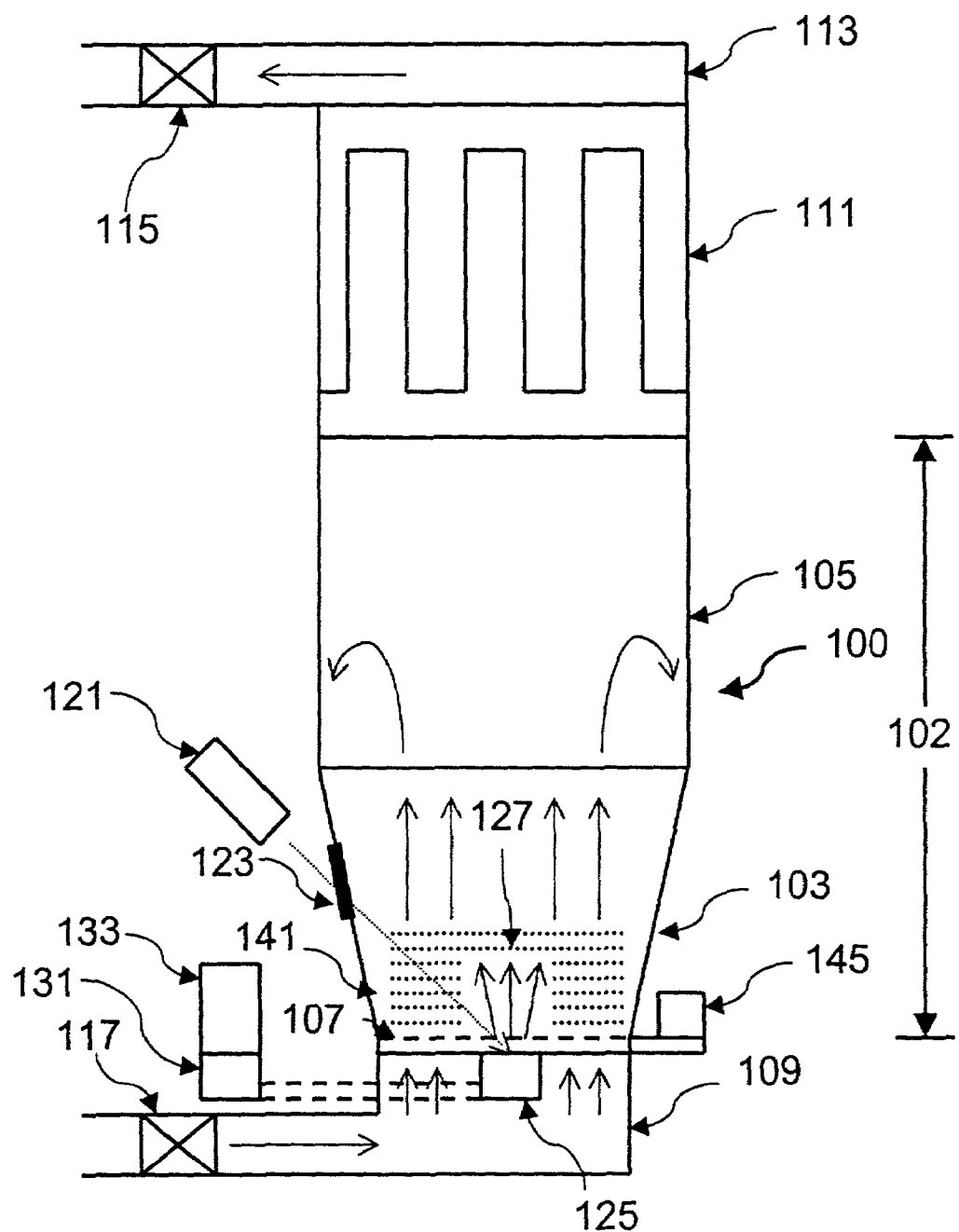
FIG. 2 is a diagrammatic representation of another embodiment of the invention.

In a preferred embodiment, and as shown in FIGS. 1 and 2, the PVD technique known as laser ablation is employed in the fabrication of the coated particles. When desirable, other PVD techniques, such as thermal evaporation or sputtering, may be utilized to produce a flux of ablated species for deposition onto a host surface. A typical laser used in the practice of the present method is a Lambda Physik model 1248 pulsed excimer gas laser with an operating UV wavelength of 248 nanometers. Many other suitable lasers may be substituted therefor, such as a Nd:YAG laser operating at 255–1064, etc. The laser beam will produce a particle flux generally perpendicular to the surface of the target.

The laser wavelength is selected based on the nature of the material to be ablated. A high absorption coefficient and low reflectivity is a factor to consider for efficient removal of the material by the ablation process. The absorption coefficient is dependent on the type of material and the laser wavelength, and in some cases the intensity of the laser beam. Typically, as the surface temperature is increased, the absorption coefficient of the material increases. Thus the selection of laser wavelength is dependent on the type and characteristics of materials ablated.

Additionally, for wavelengths in the blue and ultraviolet region of the spectrum, the absorption coefficient increases and the reflectivity decreases. Thus, although any wavelength could be used, the use of wavelengths less than 350 nm may lead to more efficient removal of the material.

Since the laser system and the PLD chamber are preferably separate, the process offers great latitude for varying experimental parameters. With the proper laser choice this process can be used to create coatings of many different materials on particulates. The composition of the coatings is dependent on the laser processing parameters, such as incident energy fluence ($J/cm^2$). laser repetition frequency, target to substrate distance, and optical absorption coefficient of the target.

In most cases the chamber will be separate from the laser. However, if one uses compact lasers like a solid-state laser operating from 248 to 1056 nm, the laser can be attached to the side of the chamber. The specific conditions which affect the deposition of coatings include (i) control of the laser influence; (ii) control of the laser spot size; (iii) control of the gas composition and flow rate; (iv) control over the pulsation rate; and (v) number of pulses and wavelength of the light. By controlling each of these parameters, which are different for different materials, the integrity, microstructure, topology, architecture, thickness and adhesion of the coatings on the drug particles can be varied.

C. Coated Particle Compositions

The coating techniques described herein and the compositions derived therefrom are applicable to a wide variety of compositions, including, but not limited to, pharmaceutical compositions for human or veterinary use, biotechnology applications, herbicides, or pesticides. Pharmaceutical compositions include organic and inorganic active compounds, including biologically active peptides, proteins, and nucleic acids. Pharmaceutical compositions of the invention may be delivered by inhalation through the respiratory tract, as well as, orally, parenterally, or transdermally. In the embodiment of an implant, or other slow release formulation, such compositions may be manually placed into a body. In addition, site specific entities may be added to the particle surface so the drug core may be carried to a specific tissue. Methods of delivery of such compositions are well known in the art, and are described, for example, in *Modern Pharmaceutics*, Second Edition, edited by Gilbert S. Banker and Christopher T Rhodes, the entire contents of which is hereby incorporated by reference.

In one embodiment, an oral drug is formulated with a thin-film coating of the present invention. Exemplary pharmaceuticals that would benefit from such a coating include drugs used in controlled or targeted release formulation, taste-masking, or particulate surface modification prior to tableting or capsule filling.

In another embodiment, a pulmonary dry-powder formulation produced with a thin-film coating of the present invention. Exemplary pulmonary drugs that could be used include glucocorticoids and other localized asthma drugs, as well as drugs and bioactive peptides and proteins for systemic delivery, such as insulin, that have low absorption through the oral route. The present methods provides a high encapsulation efficiency, reduced damage to the drug particle during coating, and do not produce coatings of a thickness that would reduce respiratory fraction.

Topical drugs that could be used include localized antibiotics, antifungals, and anti-inflammatories. Parenteral drugs that could be used include many currently used suspensions and preparations for sustained or localized release, or simply to reduce hydration and improve shelf-life of protein powders.

In illustrative embodiments, the coating material may be deposited onto the surface of the drug particle by a pulsed laser ablation process wherein the individual particulate coating materials deposited onto the core drug particles range in size from about 1 or 2 nm in average diameter up to and including about 40 or 50 nm in diameter. More preferably the particles that comprise that coating may be range in size from about 3 or 4 nm in diameter up to and including about 20 to 30 nm in diameter. In other embodiments that particles that comprise the coating may range in size from about 5 or 6 nm in diameter up to and including about 10 or 15 nm in diameter. By modifying the particular parameters of the coating process, coatings that are comprised of particles of slightly larger or smaller average diameter particle sizes, may be obtained.

Such layers do not necessarily have to be continuous in thickness over the entire surface of the drug particles, and in fact, in certain embodiments, it may be more desirable to provide substantially discontinuous deposition of the coating particles onto the surfaces of the drug particles to achieve coated drug particles that have particular pharmaceutically-desirable properties. In some cases, it may be desirable to provide coatings that are almost entirely discontinuous in thickness over the surfaces of the drug particles.

Likewise, in certain applications, it may also be desirable to coat the drug particles with mixtures of two or more coating materials. Such coating mixtures may be prepared so that each member of the plurality of coating materials may be simultaneously ablated and applied to the surfaces of the drug particles, or more conveniently, it may be desirable to alternate or sequentially apply two or more coating materials onto the surface of the drug particles to be coated. The ability of the method to prepare pluralities of layers of coating materials is particularly desirable when timed-, controlled- or sustained-release formulations are being prepared. Such combinations of coating materials may afford particular pharmaceutically desirable properties to the resulting coated drug particles. Such combinations may include both combinations of inert coating materials, or combinations of coating materials and pharmaceutically active compounds, or even multiple inert materials, and multiple drugs, or site-specific entities to produce targeting. The combinations are limited only by the choice of the user, and the compatibilities of the compounds.

The choice of core particle size, the choice of coating material(s), the size of the coating material particles, and the overall thickness and continuous/discontinous nature of the coating layer(s) will, of course, vary from particular application to application. The skilled artisan will be able to adjust such parameters to prepare coated drug particles having particular desired physical or pharmaceutical properties. The choice of these parameters will often depend upon the particular compound to be coated, and/or the particular coating to be applied to the host particle. Likewise, the preparation of the host particle may be varied depending upon the particular thickness of coating to be applied during the laser ablation process. In some circumstances, it may be necessary to dessicate, grind, pulverize, or otherwise reduce the particular core particulate materials to a certain uniform particle size or consistency prior to, or following, the deposition of the coating material(s) onto the surfaces of the host drug particles. In addition, separation and coating may be performed in a continuous fashion to reduce agglomeration and remove particles once a target size is reached (cyclone). In either embodiment, the milling of the coated or uncoated drug particles may be readily achieved using methods well known to those of skill in the pharmaceutical arts. For example, mechanical shearing or milling may be used to reduce the particles to a particular average particle size. Likewise, methods such as sieving may be employed to improve the uniformity of particle sizes in a given sample.

When desirable, no milling or sizing may be required, and in fact, the drugs to be coated may be subjected to the laser ablation processes described herein in their natural, or commercially-available state. Moreover, in some situations, it may not even be necessary to assure a particular coating particle size or a coating thickness, or even to prepare substantially continuous layers of coating material onto the surface of the drug particle, so long as the resulting coated material retains all or most of its desired characteristics.

As described above, the total thickness of the coating material(s) deposited onto the surface of the core particle may range in average thickness from about 1 nm to about 1000 nanometers. In certain embodiments, the coating particles will form one or more layers onto the surface of the drug particles, each layer having a thickness of about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 nm. In other embodiments, slightly thicker coating layers will be desired and in those instances, layers having an average thickness of about 31, about 32, about 33, about 34, about 35, about 36 about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60 nm may be useful in coating particular drug particles for use in the pharmaceutical arts. Likewise, when slightly thicker coating layers are required, layers having an average thickness of about 65, about 70, about 75, about 80, about 85, about 90, about 95, about 100, about 120, about 140, about 160, about 180, about 200, about 225, about 250, about 275, about 300, about 400, about 450, about 500, about 550, about 600, about 650, about 700, about 750, about 800, about 850, about 900, about 950, or even about 1000 nm may be desired in coating particular drug particles for use in achieving coated drug particles having certain pharmaceutically desirable properties. Of course, thicker or thinner layers may be created, if desired, by modifying the operational parameters.

As described herein, the sizes of the core drug particles to be coated may range in average diameter from about 0.1 μm to about 1000 micrometers. In certain embodiments, the host drug particles will typically have an average size of about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, or about 20 μm in average particle diameter. For some drugs, the average particle diameter may be slightly larger. As such, the method may also be employed to coat these particles as well. In these instances, the drug particles may have an average particle size of about 21, about 22, about 23, about 24, about 25, about 26, about 27, about 28, about 29, about 30, about 40, about 50, about 60, about 70, about 80, about 90, about 100, about 120, about 140, about 160, about 180, about 200, about 220, about 240, about 260, about 280, about 300, about 350, about 400, about 450, or even about 500 μm in diameter. Intermediate sizes in each of the stated size ranges may be prepared using the disclosed methods, and such intermediate sizes to fall within the scope of the present invention.

The coated drug particles of the present invention may range in size from about 0.1 μm average diameter, up to and including those coated particles that are about 2–3 mm in average particle size diameter. In certain embodiments, the final coated drug particles obtained will typically have an average particle diameter size of about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, or about 20 μm in average particle diameter. For some drugs, the average coated drug particle diameter size may be slightly larger, and may have an average size of about 21, about 22, about 23, about 24, about 25, about 26, about 27, about 28, about 29, about 30, about 40, about 50, about 60, about 70, about 80, about 90, about 100, about 120, about 140, about 160, about 180, about 200, about 220, about 240, about 260, about 280, about 300, about 350, about 400, about 450, or even about 500 μm in average diameter, and may be as large as about 0.75, about 1.0, about 1.25, about 1.5, about 1.75, about 2.0, or even about 2.5 mm in diameter.

In all cases, it is contemplated that all intermediate sizes in each of the stated size ranges may be prepared using the disclosed methods, and that such intermediate sizes to fall within the scope of the present invention.

The preferred sizes for the final coated particles will depend on the application. Generally preferred sizes for different applications will be described below.

D. Pharmaceutical Formulations Comprising Coated Drug Particles

The present invention also concerns formulations of one or more of the coated drug particle compositions disclosed herein in pharmaceutically acceptable solutions for administration to a cell or an animal, either alone, or in combination with one or more other drugs for the treatment of particular diseases or medical conditions.

The coated drug particle compositions disclosed herein may be administered in combination with other agents as well, such as, e.g., proteins or polypeptides or various pharmaceutically-active agents. As long as the composition comprises at least one of the coated drug particle compositions disclosed herein, there is virtually no limit to other components that may also be included, given that the additional agents do not cause a significant adverse effect upon contact with the target cells or host tissues. The disclosed compositions may thus be delivered along with various other agents as required in the particular instance. Such secondary compositions included in the pharmaceutical formulations may be purified from host cells or other biological sources, or alternatively may be chemically synthesized as described herein. The formulations may comprise substituted or derivatized RNA, DNA, or PNA compositions, they may also be modified peptide or nucleic acid substituent derivatives, or other coated or noncoated drugs.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In general, the pharmaceutically relevant particles/particulate materials of this invention include particles from 0.1 µm to 2–3 mm, where oral formulations include particles primarily from 10 µm to 1 or more mm, injectable powders are 80 µm to 200 µm, and inhaled or nasally delivered powders are 1 to 10 µm (inhaled: generally 1 to 5; nasal: generally 1 to 10).

The present invention has been found to be particularly suited in the coating of several specific classes of drugs, including but not limited to inhaled powders, such as glucocorticoids. Nano-thin coatings applied to dry-powder formulations improve the flow properties and provide sustained-release of already established and FDA-approved formulations without changing the bulk product or requiring remanufacturing.

Glucocorticoids are beneficial in treating various pulmonary diseases, including asthma, sarcoidosis, and other conditions associated with alveolitis. Although systemic glucocorticoid therapy is effective in such conditions, prolonged administration carries the risk of toxicity and side effects (Mutschler and Derendorf, 1995). In attempts at reducing systemic side effects, several clinically efficacious glucocorticoids, including TA, have been employed for delivery as aerosols or dry powders.

In a recent study, it was shown that beneficial pulmonary effects were achieved when three different glucocorticoid powders and suspensions are administered intratracheally in rats. (Talton, 1999). In contrast, lung targeting (ratio of local to systemic effects) was not observed when different glucocorticoids are administered intratracheally, presumably because of the fast absorption of the lipophilic steroid (Hochhaus et al., 1995). This suggests that pulmonary targeting depends on slow release from the delivery that results in a prolonged pulmonary residence time.

The use of liposomes has been suggested to provide sustained pulmonary release for various drugs including glucocorticoids such as beclomethasone diproprionate and dexamethasone (Tremblay et al., 1993; Fielding and Abra, 1992; Vidgren et al., 1995; Schreier et al., 1993). However, although liposomes have a moderate loading capacity for lipophilic glucocorticoids (10 to 20%) such as TA under equilibrium conditions, TA is rapidly released under non-equilibrium conditions from the liposome matrix upon dilution or administration (Schreier et al., 1994).

As the examples demonstrate, the present invention is particularly suited for glucocorticoid formulations.

Delivery devices such as dry powder inhalers and metered dose inhalers have been improved in the last few years such that pulmonary deposition can range from 10% for conventional delivery systems to up to 40% for recently developed third generation devices (Newman et al., 1997).

Interestingly, one of the predominant factors responsible for pulmonary targeting, the pulmonary mean residence time, has not been extensively evaluated. Pulmonary residence time is determined by the release rate of the inhaled particle from an inhaled solid (powder) or an alternative delivery system such as liposomes, the absorption rate of dissolved drug across pulmonary membranes and the mucociliary clearance which is able to remove drug particles from the upper portions of the lung. The absorption across membranes is a rapid process for lipophilic glucocorticoids (Burton and Schanker, 1974), and, consequently, the dissolution rate of a glucocorticoid powder will be the main determinant for controlling the pulmonary residence time. Simulations using a recently developed PD/PD model showed that for inhalation products with very rapid release kinetics, no targeting is observed because of the very fast absorption from the lung into the systemic circulation. With decreasing release rate (dissolution rate), pulmonary targeting is increased, as indicated by a dissociation of pulmonary and systemic receptor occupancies. A further decrease in release rate will consequently lead to a decrease in pulmonary targeting as a significant portion of the drug is removed via the mucociliary clearance and after swallowing is available for oral absorption. Thus, inhaled glucocorticoids should possess certain dissolution or release characteristics in order to show significant targeting.

However, this invention is suitable in preparing all forms of pharmaceutical preparations, some of which are discussed below.

1. Oral Delivery

The pharmaceutical compositions disclosed herein may be delivered by oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The coated drug particle-containing compounds may even be incorporated with excipients and used in the form of ingestible tablets, buccal tables, troches, capsules, elixirs, suspensions, syrups, wafers, and the like (Mathiowitz et al., 1997; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In additions the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 95% or 98% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

2. Injectable Delivery

Alternatively, the pharmaceutical compositions disclosed herein may be administered parenterally, intravenously, intramuscularly, or even intraperitoneally, as described in U.S. Pat. No. 5,543,158, U.S. Pat. No. 5,641,515 and U.S. Pat. No. 5,399,363 (each specifically incorporated herein by reference in its entirety). Solutions of the active compounds as free-base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences* 15th Edition, pages 1035–1038 and 1570–1580, which pages are hereby incorporated by reference). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques which yield a powder of the active ingredient plus any additional desired ingredient from a previously sterile-filtered solution thereof.

The drug compositions to be coated by the methods disclosed herein may be formulated either in their native form, or in a salt form. Pharmaceutically-accepted salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that are not intended to produce an allergic or similar unexpected reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified. Immunogenic compositions, such as vaccines, which are intended and expected to induce an immune response are, of course, pharmaceutically-acceptable.

3. Nasal Delivery

The administration of the pharmaceutical compositions by intranasal sprays, inhalation, and/or other aerosol delivery vehicles is also contemplated. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The delivery of aerosol formulations of the drugs of the present invention may be accomplished using methods such as those described in U.S. Pat. No. 5,849,265 and U.S. Pat. No. 5,922,306 (each specifically incorporated herein by reference in its entirety).

Particularly preferred medicaments for administration using aerosol formulations in accordance with the invention include, but are not limited to, anti-allergics, bronchodilators, and anti-inflammatory steroids used in the treatment of respiratory disorders such as asthma and the like.

Medicaments which may be coated and administered in aerosol formulations according to the present invention include any drug useful in inhalation therapy which may be presented in a form which is substantially completely insoluble in the selected propellant. Appropriate medicaments may thus be selected from, for example, analgesics (codeine, dihydromorphine. ergotamine, fentanyl, morphine and the like); anginal preparations; antiallergics (cromoglycate, ketotifen, nedocromil and the like); anti-infectives (cephalosporins, penicillins, rifampicin, streptomycin, sulfonamides, macrolides, pentamidines, tetracyclines and the like); antihistamines (methapyrilene and the like); anti-inflammatories (flunisolide, budesonide, tipredane, triamcinolone acetonide, and the like); antitussives (noscapine and the like); bronchodilators (ephedrine, adrenaline, fenoterol, fomloterol, isoprenaline, metaproterenol, phenylephrine, phenylpropanolamine, pirbuterol, reproterol, rirniterol, terbutaline, isoetharine, tulobuterol, orciprenaline, and the like); diuretics (amiloride and the like); anticholinergics (ipratropium, atropine, oxitropium and the like); hormones (cortisone, hydrocortisone, prednisolone and the like); xanthines (including aminophylline, choline theophyllinate, lysine theophyllinate, and theophylline); and therapeutic proteins and peptides (e.g., insulin or glucagons).

One of ordinary skill in the art will appreciate that in certain circumstances, the coated drugs particles of the present invention may be formulated in the form of salts (such as alkali metal or amine salts or as acid addition salts) or as esters (e.g., lower alkyl esters) or as solvates (e.g., hydrates) to optimize the activity and/or stability of the medicament and/or to minimize the solubility of the medicament in the delivery vehicle or propellant.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly the present invention farther provides aerosol formulations that contain two or more particulate medicaments that are coated using the methods of the present invention. The medicaments may be selected from suitable combinations of the drugs mentioned herein, such as budesonide (BUD), triamcinolone acetonide (TA), fluticasone propionate (FP), and the like, or may even include suitable combinations of other bronchodilatory agents (including ephedrine and theophylline. fenoterol, ipratropium, isoetharine, phenylephrine, and the like).

Preferred aerosol formulations in accordance with the invention comprise an effective amount of a polymer-coated particulate pulmonary medicament and a fluorocarbon or hydrogen-containing chlorofluorocarbon propellant. The final aerosol formulation may typically contain from about 0.005% to about 10% (wt./wt.) of the coated drug particles, more preferably from about 0.05% to about 5% (wt./wt.) of the coated drug particles, and more preferably still, from about 0.1% to about 3.0% (wt./wt.), of the coated particles relative to the total weight of the formulation.

The propellants for use in the invention may be any fluorocarbon or hydrogen-containing chlorofluorocarbon or mixtures thereof as described in U.S. Pat. No. 5,922,306.

4. Additional Modes of Drug Delivery

In addition to the methods of delivery described above, the following techniques are also ii contemplated as alternative methods of delivering coated drug particle compositions. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783, 208) and feed back-controlled delivery (U.S. Pat. No. 5,697,899), each specifically incorporated herein by reference in its entirety.

E. Coating Compositions

The target materials used for the coating include most solids currently used in the pharmaceutical and food industries, namely any material that can be effectively ablated by the energy source. These materials include, but are not limited to, biodegradable and biocompatible polymers, polysaccharides, and proteins. Suitable biodegradable polymers include polylactides, polyglycolides, polycaprolactones, polydioxanones, polycarbonates, polyhydroxybutyrates, polyalkylene oxalates, polyanhydrides, polyamides, polyesteramides, polyurethanes, polyacetates, polyketals, polyorthocarbonates, polyphosphazenes, polyhydroxyvalerates, polyalkylene succinates, poly(malic acid), poly (amino acids), polyvinylpyrrolidone, polyethylene glycol, polyhydroxycellulose, polyorthoesters, and combinations thereof, as well as other polylactic acid polymers and copolymers, polyorthoesters, and polycaprolactones, etc. Suitable biocompatible polymers include polyethyleneglycols, polyvinylpyrrolidone, and polyvinylalcohols, etc. Suitable polysaccharides include dextrans, cellulose, xantham, chitins and chitosans, etc. Suitable proteins include polylysines and other polyamines, collagen, albumin, etc. A number of materials particularly useful as coating materials are disclosed in U.S. Pat. No. 5,702,716.

F. Substrates for Coating

The core particles are generally large relative to the size of the coating particles or particulate materials, with the method proven to be very applicable to core particles sized from about 0.1 to about 1000 microns. It is understood that the core particulate materials, i.e., core particles, can be smaller, down to several nanometers in diameter, or larger, up to several millimeters in diameter. The core particulate materials are retained within a processing container that has a large enough volume to permit movement of the particles within the container. The top of the container is open or covered by a mesh to prevent the powder from escaping, and the container maintained in a vertical position during fluidization, or a portion of the processing container, such as a part or all of a side or bottom, is provided with openings or apertures to retain the core particulate materials within the processing container, if the particle deposition is to occur laterally or from below.

The core particulate material should be agitated or fluidized in some manner to expose the entire surface of each host particle to the coating particles entering the processing container to insure general uniformity of coating and to assist in the prevention of agglomeration of individual core particulate material. This fluidization may be accomplished in a number of equivalent manners, such as by mechanical agitation by vibration, rotation or movement of the processing container, by providing a stirring device within the container, preferably by pneumatic agitation by passing gas flow through the core particulate material. Mechanisms for fluidizing particles are well known in the art and examples are described in *Fluidization* (Grace and Matsen, eds., Plenum Press, NY 1980), which is hereby incorporated by reference.

The percentage of deposition or coverage of the coating particles on the core particulate material is controlled by controlling the size of the coating particles and the treatment time. The longer the treatment time, the more coating particles will be adhered to the surface of the core particulate material, increasing both the percentage of coverage and the thickness of the coating layer. Surface coverage can be adjusted from below 1 percent up to 100 percent. The size of the coating particles is controlled by the atmospheric composition. Inert gases such as helium, argon, or nitrogen, etc., are preferred, but reactive gases may be used. Reactive gases such as oxygen, ammonia or nitrous oxide produce higher concentrations of molecular, as opposed to atomic, species within the ablated particle flux, and are used if deposition of oxide, nitride or similar particles is desired.

Pressure within the system is generally around atmospheric pressure, i.e., about 1 atmosphere, or about 760 Torr. However, pressure may vary to some extent, and may be as low as about 10 Torr to as high as about 2500, or any pressure in between. Preferably, the pressure in the coating chamber is greater than about 20, or 30, or 40, or 50 Torr, more preferably greater than about 100 or 500 Torr, and most preferably greater than about 700 Torr. Preferably, the pressure in the coating chamber is less than about 1000, more preferably less than about 900, and most preferably less than about 820. In a most preferred embodiment, the pressure in the coating chamber is about 760 Torr, or atmospheric pressure. Within these ranges, and around these values, the pressure may be varied.

K. Microencapsulation

The area of microencapsulation is relatively new, previously limited to solvent evaporation techniques (Thies, 1982; Manekar et al., 1992; Conti et al., 1992). Currently there are several different ways of applying coatings to particles in industry, mainly through spray-coating technologies (Gopferich et al., 1994). Pranlukast, a leukotriene inhibitor, encapsulated with hydroxypropylmethylcellulose (HPMC) nanospheres prepared by spray drying showed an improvement in inhalation efficiency but did not show a significant difference in the dissolution rate (Kawashima et al., 1998). The disadvantages of applying micron-thick coatings for sustained-release (10–100 microns thick) (Glatt, 1998) is that large quantities of solvents must be dried under strong venting and that an increase in particle size reduces the inhalation efficiency (Zeng et al., 1995; Talton, 1999).

L. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Matrix Target Solid Target at Room Temperature

The required biocompatible coating material (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) can be combined with N number of constituent (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) materials to form solid matrix target (SMT) for coating core particles. The overall properties of the constituent materials must reflect a higher absorption coefficient with respect to the EORS process, thereby interaction with the bio-coating material is reduced, thereby allowing transfer to the fluidized core particles without negative effects. Alternatively the above said constituent materials may also be altered chemically during interaction with the EORS process to further facilitate the efficiency of the core particle coating process. Depending on the composition and the removal rate of the constituent materials involved, removal of the constituents for toxicity purposes may or may not be necessary.

Example 1

Triamcinolone acetonide (TA) was coated with a solid PLGA target for various times under low fluidization. Films were deposited onto glass slides before powder runs to characterize the deposited film material.

PLGA was deposited onto copper TEM grids at atmospheric pressure and a Joel 200 TEM was used to observe nanoparticle size and composition. The results are shown in FIG. 3, which shows a transmission electron microscope (TEM) image of deposited nanoparticles film at atmospheric pressure (scale 100,000 times). FIG. 4 shows another TEM image of deposited nanoparticles film at atmospheric pressure (scale 100,000 times).

Spherical PLGA nanoparticles from 20 nanometers and below are observable at 100,000 times magnification. The particles were dispersed uniformly across the substrate after only 5 pulses from the laser at 750 $mJ/cm^2$.

Characterization above shows the versatility of the coating process showing characterization of original PLGA, HPMC, Eudragit 4135, and SDS. Characterization using NMR shows a strong correlation of deposited material characteristic peaks to original material (FIG. 5). The deposition rate of PLGA under optimized conditions also shows a slightly higher deposition rate near atmospheric pressure compared to low pressures (FIG. 6). Gel permeation chromatography (GPC) of original PLGA compared to ablated PLGA is shown in FIG. 7. Scanning electron microscope (SEM) analysis of PLGA coatings on TA powders shows no increase in particle size compared to original TA powders, verifying the relative nanometer thin coating thicknesses obtainable by this process (FIGS. 8 and 9). Finally, the sustained-release profile of PLGA coated TA is shown compared to original TA with powders coated for 30 minutes providing 12 to 24 hour release in vitro (FIG. 10). Other coating materials including poly-vinyl-pyrollidone (PVP), polyethylene glycol (PEG), amylopectin starch, albumin protein, and chitin have also been deposited successfully.

Example 2

PLGA coatings on Bovine Serum Albumin (BSA) were successful in sustaining the release out to 2 to 3 hours. BSA powders were sieved and the 75 to 250 micron fraction was coated with poly(lactic-co-glycolic acid) (PLGA) for 30 minutes. Dissolution on 20 mg coated and uncoated powders were performed in triplicate in 40 ml isotonic saline in centrifuge tubes on a rotating tumbler at room temperature. Filtered samples were collected at different time points up to 12 hours and analyzed using the Biocinchoninic Acid (BCA) protein assay in a 96-well plate and plate-reader at 568 nm. The results are presented in FIG. 11.

Example 3

Another accepted material used in oral tablet dosage forms is the different celluloses, such as hydroxy-propyl-methyl-cellulose (HPMC). Coatings of HPMC were deposited on flat glass slides for characterization and then onto micronized TA powders for 30 minutes. FIG. 12 shows proton NMR spectra of the original HPMC and HPMC deposited at 500 $mJ/cm^2$ near atmospheric pressure (10 Torr). For HPMC, it is believed that the 3.6 ppm peak correlates to the methyl protons and the multiple peaks at 6.0 ppm for the multiple ring protons.

FIG. 13 shows dissolution test results for coated and uncoated TA powders. Coated formulations showed 80% release after 2 to 4 hours for HPMC coatings compared to 24 hours for PLGA coatings, but additionally showed improved flow properties as seen by Anderson Cascade Impaction.

Example 4

Another accepted material used in oral tablet dosage forms is the poly(acrylic acids), such as Eudragit (Rohm), which show specific pH sensitive release. Intact coatings of Eudragit were successfully deposited on flat glass slides for characterization. Proton NMR spectra of original Eudragit compared to deposited Eudragit are shown in FIG. 14.

Example 5

A surfactant material used in oral tablet dosage forms to increase solubility and flowability is sodium-dodecyl-sulfate (SDS). Intact coatings of SDS were successfully deposited on flat glass slides for characterization. Proton NMR spectra of original SDS compared to deposited SDS are shown in FIG. 15.

In addition, Anderson Cascade Impaction, which measures the deposition of powders onto different stages based on the aerodynamic particle size, and SDS coated TA powders, was performed. Results, shown in FIG. 16, showed a nearly double increase in emitted powder dose compared to uncoated powders, suggesting a higher flowability and deposition into the lung.

Example 6

PLGA coatings on Griseofulvin (GRIS), an oral fungistatic, were successful in sustaining the release out to 12 to 24 hours. GRIS powders were coated with poly(lactic-co-glycolic acid) (PLGA) for 30 minutes at atmospheric pressure under helium flow and mechanical agitation. Dissolution of 50 mg coated and uncoated powders were performed in a USP dissolution bath (paddles, 50 RPM) in pH 7.4 phosphate buffer with 0.5% SDS at 37 degrees C. Filtered samples were collected at different time points up to 24 hours and analyzed using HPLC. The results are presented in FIG. 17.

Example 7

PLGA coatings on bupivacaine-HCl (BUP), a pain-blocking injectable, were successful in sustaining the release out to 2 to 4 hours. GRIS powders were coated with poly(lactic-co-glycolic acid) (PLGA) for 30 minutes at atmospheric pressure under helium flow and mechanical agitation. Dissolution of 4 mg coated and uncoated powders were analyzed in triplicate in 40 ml isotonic saline in centrifuge tubes on a rotating tumbler at room temperature. Filtered samples were collected at different time points up to 12 hours and analyzed at 220 nm in a Beckman UV spectrophotometer. The results are presented in FIG. 18.

Example 8

Figure 19:
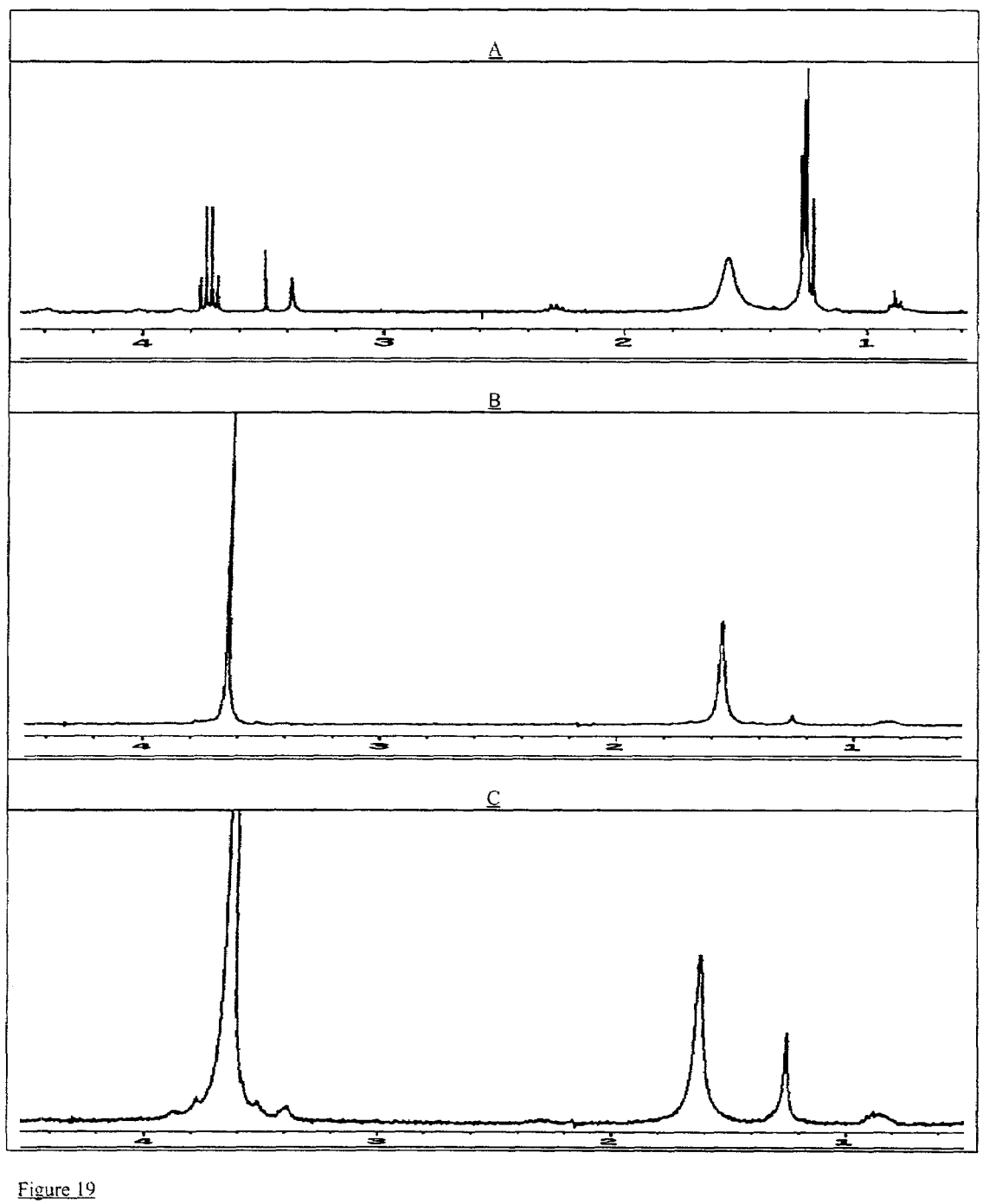

Using a solid matrix of PEG 20,000, phosphatidylcholine (PC), a lipid present in cell membranes, was deposited successfully onto flat glass slides for characterization. Proton NMR spectra of the A) original PC, B) original PEG400, and C) deposited PEG400/PC at 500 mJ/cm$^2$ for 10 minutes are shown in FIG. 19.

2. Matrix Target Liquid at Room Temperature

The required biocompatible coating material (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) can be combined with N number of constituent (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) materials to form a liquid matrix target (LMT) for coating core particles. The overall properties of the constituent materials must reflect a higher absorption coefficient with respect to the EORS process, thereby interaction with the bio-coating material is reduced, allowing transfer to the fluidized core particles without negative effects. Although the target material is a liquid, interaction with EORS during a time regime on the order of nano-microseconds allows the following events to occur:

1) Heating of laser interaction area (LIA).
2) Subsequent curing and preferential absorption with respect to the biocoating and constituent materials.
3) Evaporation of the bio-coating material and coating onto the core particles.

Alternatively the above said constituent materials may also be altered chemically during interaction with the EORS process to further facilitate the efficiency of the core particle coating process. Depending on the composition and the removal rate of the constituent materials involved, removal of the constituents for toxicity purposes may or may not be necessary.

Example 9

Figure 20:
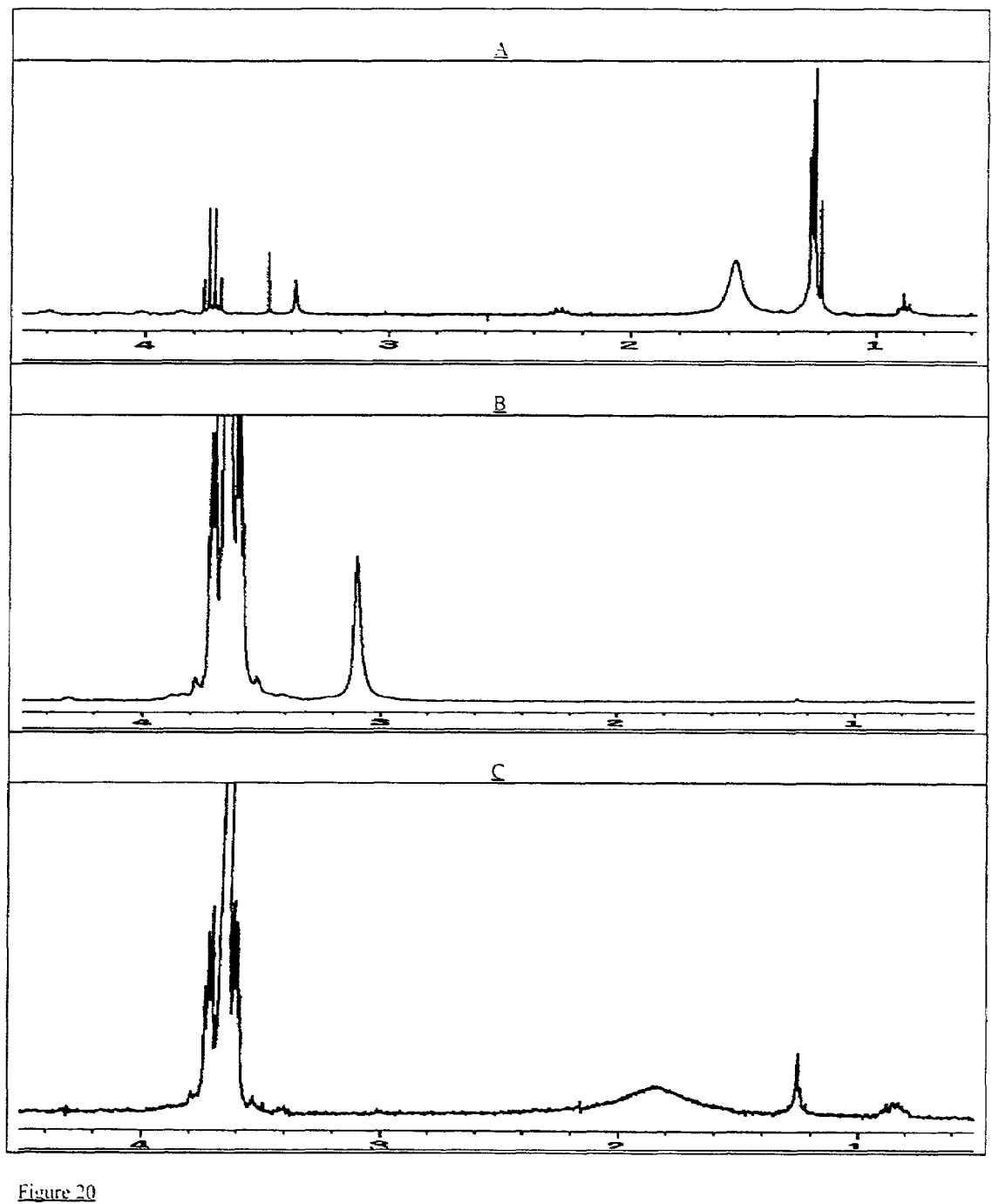

Using a liquid matrix target of PEG 400, phosphatidylcholine (PC), a lipid present in cell membranes, was deposited successfully onto flat glass slides for characterization. Proton NMR spectra of the A) original PC, B) original PEG400, and C) deposited PEG400/PC at 500 mJ/cm$^2$ for 10 minutes are shown in FIG. 20.

3. Matrix Target Solid-Liquid Target at Room Temperature

The required biocompatible coating material (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) can be combined with N number of constituent (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) materials to form a gel matrix target (GMT) for coating core particles. The overall properties of the constituent materials must reflect a higher absorption coefficient with respect to the EORS process, thereby interaction with the bio-coating material is reduced, thereby allowing transfer to the fluidized core particles without negative effects. The difference that must be identified between cases two and three are the following:

1) The functionality is based on solid material absorption being different than the liquid counterpart, constituent or bio-coating material.
2) The above said solid material may precipitate out of the liquid solution during the reaction via catalyst type reactions, constituent or bio-coating material.
3) The constituent material will control the interaction processes associated with the EORS.

Although the target material may be a solid or a solid/liquid composite, interaction with EORS during a time regime on the order of nano-microseconds allows the following events to occur:

1) Heating of laser interaction area (LIA).
2) Subsequent curing and preferential absorption with respect to the biocoating and constituent materials. In the case of the liquid pure liquid, solid constituent materials may precipitate out of solution to act as selective absorption sites, chromophores, nano-particles or entities.
3) Evaporation of the bio-coating material and coating onto the core particles.

Alternatively the aforementioned constituent materials may also be altered chemically during interaction with the EORS process to further facilitate the efficiency of the core particle coating process. Depending on the composition and the removal rate of the constituent materials involved, removal of the constituents for toxicity purposes may or may not be necessary.

Example 10

Figure 21:
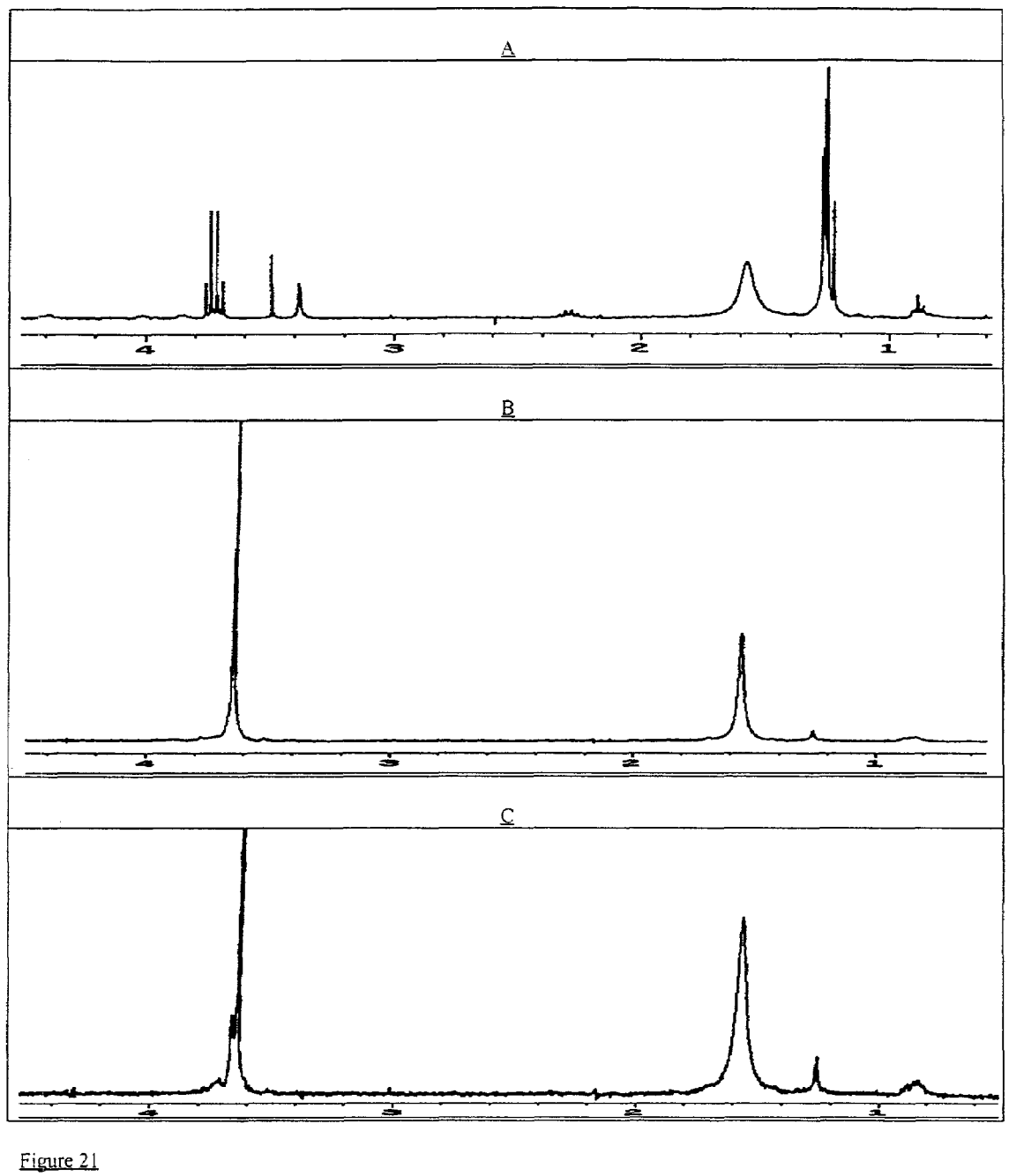

Using a gel matrix of PEG 20,000, phosphatidyl choline (PC) (mixed with PEG20K at 60° C.) was deposited successfully after cooling onto flat glass slides for characterization. Proton NMR spectra of the A) original PC, B) original PEG20K, and C) deposited PEG20K/PC gel at 500 mJ/cm$^2$ for 10 minutes are shown in FIG. 21.

4. Matrix Target Solid Below Room Temperature

The required biocompatible coating material (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) can be combined with N number of constituent (bioactive ceramics, anionic or cationic polymers or lipids, antibodies, or antigens, bio-polymers, drugs, proteins, sugars, lipids, electronic polymers, SMART polymers, functional organic molecules, metastable compounds and biologically inactive materials) materials to form a frozen matrix target (FMT) below room temperature (<300 K) for coating core particles. The overall properties of the constituent materials must reflect a higher absorption coefficient with respect to the EORS process, thereby interaction with the bio-coating material is reduced, thereby allowing transfer to the fluidized core particles without negative effects.

Although the target material may be a solid or a solid/liquid composite, interaction with EORS during a time regime on the order of nano-microseconds allows the following events to occur:

1) Heating of laser interaction area (LIA).
2) Preferential absorption with respect to the bio-coating and constituent materials.

3) Evaporation of the bio-coating material and coating onto the core particles.

Alternatively the above said constituent materials may also be altered chemically during interaction with the EORS process to further facilitate the efficiency of the core particle coating process. Depending on the composition and the removal rate of the constituent materials involved, removal of the constituents for toxicity purposes may or may not be necessary.

Example 11

Using, a frozen matrix of PEG 400, phosphatidylcholine (PC) was snap frozen in liquid $N_2$ and deposited successfully onto flat glass slides for characterization. Proton NMR spectra of the A) original PC, B) original PEG20K, and C) deposited PEG20K/PC gel at 500 mJ/cm$^2$ for 10 minutes are shown in FIG. 22.

VI. Cited Documents

The following literature citations as well as those cited above are incorporated in pertinent part by reference herein for the reasons cited in the above text:

Agarwal and Phadke, "Laser assisted deposition of supramolecular organizates on solid surfaces" Mat Sci Eng C, 6:13–17, 1998.

Banker and Rhodes, Eds, Modern Pharmaceutics, Marcel Dekker, Inc., New York 1990.

Bourlais, et al., "Ophthalmic drug delivery systems—recent advances", Prog Retin Eye Res, 17(1): 33–58, 1998.

Burton and Schanker, "Absorption of corticosteroids from the rat lung," Steroids, 23(5):617–24, 1974.

Conti, Pavanetto and Genta, "Use of polylactic acid for the preparation of microparticulate drug delivery systems," J. Microencapsul., 9(2): 153–66, 1992.

Fielding and Abra, "Factors affecting the release rate of terbutaline from liposome formulations after intratracheal instillation in the guinea pig," Pharm. Res., 9(2):220–23, 1992.

Glatt, "Multi-purpose Fluid Bed Processing," Product Literature, 1998.

Gopferich, A., Alonso, M., and Langer, R., "Development and characterization of of microencapsulated microspheres", Pharm Res, 11(11): 1568–74, 1994.

Herdan, G., Small Particle Statistics, Second Edition, Butterworths, London, 1960.

Hochhaus, Derendorf, Möllmann and Gonzalez-Rothi, "Pharmacokinetic/pharmacodynamic Aspects of Aerosol Therapy Using Glucocorticoids as a Model," J. Clin. Pharmacol., 37:881–92, 1997.

Hochhaus, Gonzalez-Rothi, Lukyanov, Derendorf, Schreier and Dalla Costa, "Assessment of glucocorticoid lung targeting by ex-vivo receptor binding studies," Pharm. Res., 12:134–37, 1995.

Huang, Tamada, Hochhaus and Bodor, "An AM1-based model for the estimation of the relative binding affinity for glucocorticoids," in "1$^{st}$ Drug Optimization via Retrometabolism Conference," Amelia Island: Die Pharmazie, 1997.

Kawashima, Serigano, Hino, Yamamoto and Takeuchi, "A new powder design method to improve inhalation efficiency of pranlukast hydrate dry powder aerosols by surface modification with hydroxypropylmethylcellulose phthalate nanospheres," Pharm. Res., 15(11):1748–52, 1998.

Kodas, T and Hampden-Smith, M., Aerosol Processing of Materials, Wiley-VCH, New York, 1999.

Manekar, Puranik and Joshi, "Microencapsulation of propranolol hydrochloride by the solvent evaporation technique," J. Microencapsul., 9(1):63–66, 1992.

Mathiowitz, et. Al., "Biologically erodable microspheres as potential oral drug delivery systems", Nature, 386(6623): 410–4, 1997.

Mutschler and Derendorf, in "Drug Actions," CRC Press, Boca Raton, Fla., pp. 286–87, 1995.

Newman, Steed, Reader, Hooper and Zierenberg, "Efficient delivery to the lungs of flunisolide aerosol from a new portable hand-held multidose nebulizer," J. Pharm. Sci., 85:960–64, 1997.

Ogale, S. B., "Deposition of Polymer Thin Films by Laser Ablation," in Pulsed Laser Deposition of Thin Films, Chrisey, D. B. and Hubler, G. K., Eds. John Wiley & Sons, New York, 1994, Chapter 25.

Schreier, Gonzalez-Rothi and Stecenko, J. Control Release, 24:209–23, 1993.

Schreier, Lukyanov, Hochhaus and Gonzalez-Rothi, "Thermodynamic and kinetic aspects of the interaction of triamcinolone acetonide with liposomes," Proceed. Inter. Symp. Control. Rel. Bioact. Mater., 21:228–29, 1994.

Takenaga, M., et.al., "Microparticle resins as a potential nasal drug delivery system for insulin", J Controlled Release, 52(1–2): 81–7, 1998.

Talton, James D., Ph.D. Thesis, University of Florida, 1999.

Thies, "Microcapsules as drug delivery devices," Crit. Rev. Biomed. Eng., 8(4):335–83, 1982.

Tremblay, Therien, Rocheleau and Cormier, Eur. J. Clin. Inv., 23:656–61, 1993.

Vidgren, Waldrep, Arppe, Black, Rodarte, Cole and Knight, "A study of $^{99m}$technetium-labeled beclomethasone diproprionate dilauroylphosphatidylcholine liposome aerosol in normal volunteers," Int. J. Pharm., 115:209–16, 1995.

Zeng, Martin and Marriott, "The Controlled Delivery of Drugs to the Lungs," Int. J. Pharm., 124:149–64, 1995.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A fluidized bed coating apparatus for coating core particles by ablation of a coating material, comprising:
   (a) a coating chamber configured to receive core particles as a substrate intended to be coated, comprising at least one wall;
   (b) a transparent window located within the wall of the coating chamber;
   (c) a matrix target located within the coating chamber, comprising a coating material;
   (d) a gas distributor configured to fluidize the core particles within the chamber by passing gas flow through the core particles; and (e) a laser configured to ablate the coating material by directing energy through the transparent window toward the matrix target, wherein the apparatus is configured to coat the core particles at a pressure higher than 10 Torr.

2. The coating apparatus according to claim 1, wherein the laser is a pulsed laser.

3. The coating apparatus according to claim 1, wherein the coating material is located at a position higher than the laser.

4. The coating apparatus according to claim 1, wherein the coating material is located at a position lower than the laser.

5. The coating apparatus according to claim 1, wherein the transparent window comprises a quartz window.

6. The coating apparatus according to claim 1, further comprising an exhaust port.

7. The coating apparatus according to claim 1, further comprising a mechanical agitator.

8. The coating apparatus according to claim 7, wherein the mechanical agitator comprises a rotational agitator.

9. The coating apparatus according to claim 7, wherein the mechanical agitator comprises a vibrational agitator.

10. The coating apparatus according to claim 1, further comprising a temperature controller.

11. The coating apparatus according to claim 1, wherein the coating chamber is configured to accept an inert gas selected from helium, argon, and nitrogen.

12. The coating apparatus according to claim 1, wherein the coating chamber is configured to accept a reactive gas selected from oxygen, ammonia, and nitrous oxide.

13. The coating apparatus according to claim 1, further comprising a filter assembly.

14. The coating apparatus according to claim 1, wherein the coating chamber includes a feeder.

15. The coating apparatus according to claim 1, wherein the coating chamber includes an exit port.

16. The coating apparatus according to claim 1, wherein the coating chamber includes a feeder and an exit port.

17. The coating apparatus according to claim 16, wherein the feeder is for introducing particles to be coated or re-coated, and the exit port is an outlet for coated particles.

18. The coating apparatus of claim 1, wherein the coating on the fluidized core particles is substantially uniform.

19. The coating apparatus of claim 1, wherein the coating on the fluidized core particles is substantially non-porous.

20. The coating apparatus of claim 1, wherein the apparatus is configured to coat fluidized core particles at a pressure between 10 Torr up to or including 760 Torr.

21. The coating apparatus of claim 1, wherein the apparatus is configured to coat fluidized core particles at about 760 Torr.

* * * * *